United States Patent
Noblett et al.

(10) Patent No.: US 11,751,912 B2
(45) Date of Patent: Sep. 12, 2023

(54) EXTERNAL FIXATION STRUT

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Andrew Phillip Noblett, Bartlett, TN (US); Johnny Mason, Bartlett, TN (US)

(73) Assignees: SMITH & NEPHEW, INC., Memphis, TN (US); SMITH & NEPHEW PTE. LIMITED, Singapore (SG); Smith & Nephew Orthopaedics AG, Zug (CH)

( * ) Notice: Subject to any disclaimer, the term of this patent is extended or adjusted under 35 U.S.C. 154(b) by 0 days.

(21) Appl. No.: 17/442,479

(22) PCT Filed: Mar. 20, 2020

(86) PCT No.: PCT/US2020/023852
§ 371 (c)(1),
(2) Date: Sep. 23, 2021

(87) PCT Pub. No.: WO2020/198005
PCT Pub. Date: Oct. 1, 2020

(65) Prior Publication Data
US 2022/0160399 A1    May 26, 2022

Related U.S. Application Data

(60) Provisional application No. 62/823,844, filed on Mar. 26, 2019.

(51) Int. Cl.
*A61B 17/64* (2006.01)
*A61B 90/00* (2016.01)
*A61B 17/66* (2006.01)

(52) U.S. Cl.
CPC ........ *A61B 17/6475* (2013.01); *A61B 17/645* (2013.01); *A61B 17/6416* (2013.01);
(Continued)

(58) Field of Classification Search
CPC . A61B 17/6475; A61B 17/62; A61B 17/6416; A61B 17/645; A61B 17/66;
(Continued)

(56) References Cited

U.S. PATENT DOCUMENTS 8,574,232 B1    11/2013    Ross et al.
10,856,908 B2  12/2020    Mullaney
(Continued)

FOREIGN PATENT DOCUMENTS

EP    2700370 A2    2/2014
EP    2774562 A1    9/2014
(Continued)

OTHER PUBLICATIONS

International Search Report and Written Opinion for International Application No. PCT/US2020/023852, dated Jun. 22, 2020.

*Primary Examiner* — Eduardo C Robert
*Assistant Examiner* — David C Comstock
(74) *Attorney, Agent, or Firm* — KDW Firm PLLC

(57) ABSTRACT

An external fixation strut and corresponding systems and methods of use with a bone alignment device are disclosed. The external fixation strut may provide an enhanced range of adjustable lengths and may be connected to a bone alignment device, thereby enabling the bone alignment device to be used over a larger workable range. As a result, comfort of a patient may be improved as the need to switch out the external fixation strut may be prevented. The external fixation strut may also include a single measurement scale that
(Continued)

may be easily viewed and used to adjust the length of the external fixation strut, thereby ensuring more accurate length adjustments.

20 Claims, 31 Drawing Sheets

(52) U.S. Cl.
CPC .............. *A61B 17/66* (2013.01); *A61B 90/06* (2016.02); *A61B 2090/061* (2016.02)

(58) Field of Classification Search
CPC ... A61B 90/06; A61B 2090/061; A61B 17/64; A61B 17/6425; A61B 17/6441; A61B 17/6458; A61B 17/6466; A61B 17/6491; A61B 2017/681; A61B 17/60
USPC ........................................................ 606/56
See application file for complete search history.

(56) References Cited

U.S. PATENT DOCUMENTS

| | | |
|---|---|---|
| 10,874,433 B2 | 12/2020 | Mannanal |
| 2009/0198234 A1 | 8/2009 | Knuchel et al. |
| 2009/0312757 A1 | 12/2009 | Kehres et al. |
| 2010/0137875 A1* | 6/2010 | Marino .............. A61B 17/7037 606/104 |
| 2010/0312243 A1 | 12/2010 | Ross et al. |
| 2010/0331840 A1 | 12/2010 | Ross et al. |
| 2011/0208187 A1 | 8/2011 | Wong |
| 2012/0303028 A1 | 11/2012 | Wong |
| 2013/0123784 A1 | 5/2013 | Ross et al. |
| 2013/0253513 A1 | 9/2013 | Ross et al. |
| 2013/0338713 A1 | 12/2013 | Kawakami et al. |
| 2014/0046326 A1 | 2/2014 | Wong |
| 2014/0135764 A1 | 5/2014 | Ross et al. |
| 2014/0276817 A1* | 9/2014 | Murray ................ A61B 17/62 606/56 |
| 2015/0265313 A1 | 9/2015 | Wong |
| 2015/0313641 A1 | 11/2015 | Ross et al. |
| 2016/0030085 A1 | 2/2016 | Ross et al. |
| 2018/0214181 A1 | 8/2018 | Mannanal |
| 2018/0368888 A1 | 12/2018 | Wigginton et al. |
| 2019/0231394 A1* | 8/2019 | Bechtel ................ A61B 17/708 606/90 |
| 2021/0085368 A1 | 3/2021 | Mannanal |

FOREIGN PATENT DOCUMENTS

| | | |
|---|---|---|
| WO | 2009018349 A2 | 2/2009 |
| WO | 2014159824 A2 | 10/2014 |
| WO | 2017/139517 A1 | 8/2017 |

* cited by examiner

200

200

204

210

208

206

2402

206

206

206

EXTERNAL FIXATION STRUT

CROSS-REFERENCE TO RELATED APPLICATIONS

This application is a National Phase filing of International Application No. PCT/US2020/023852, filed Mar. 20, 2020, which is a non-provisional of, and claims the benefit of the filing date of, U.S. provisional patent application No. 62/823,844, filed Mar. 26, 2019, entitled "External Fixation Strut," each application is incorporated by reference herein in its entirety.

FIELD OF THE DISCLOSURE

The present disclosure relates generally to orthopedic devices, systems, and methods for facilitating fracture alignment, and particularly to a strut for use with an external fixation system, the strut being arranged and configured to provide an increased range of adjustment while retaining a single measurement scale.

BACKGROUND OF THE DISCLOSURE

People suffer bone fractures each year. In many instances, a person that suffers a bone fracture is required to use a bone alignment device such as, for example, an external fixator, to align two or more bones or pieces of bone. The bone alignment device often has multiple struts that have adjustable lengths that are to be adjusted regularly (e.g., daily) in accordance with a treatment plan or prescription (used interchangeably herein without the intent to limit). The prescription specifies strut length adjustments to be made over time to ensure successful bone alignment.

Generally, each strut of a bone alignment device is attached to two displaced rings or bases of the bone alignment device. As the lengths of the struts are adjusted, the rings of the bone alignment device may be brought closer together or moved further apart. The treatment plan or prescription typically requires the spacing of the rings of the bone alignment device to have a large workable range including a very small minimum distance apart and a very large maximum distance apart. Many struts are unable to meet the entire workable range specified by the treatment plan or prescription. As a result, the struts of a bone alignment device are often changed out one or more times with new struts to accommodate the full workable range of the bone alignment device specified by the treatment plan or prescription. Changing out the struts of a bone alignment device requires a clinic visit and may be uncomfortable to the patient.

To avoid changing out struts, some commercially available struts have extended telescopic bodies that allow for large workable ranges. These struts, however, suffer from significant drawbacks including, for example, the necessity for multiple measurement scales, complicated patient prescriptions, and the need for clinical visits to controllably reconfigure the telescopic components, thereby presenting challenges to both surgeons and patients.

Thus, it would be beneficial to provide a strut for a bone alignment device that has a large workable range of adjustable lengths to accommodate a treatment plan or prescription while retaining a single measurement scale to ensure length adjustments are easy to complete without additional clinical visits for strut size changes or reconfiguring.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides an external fixation strut. The external fixation strut may be attached to or form part of a bone alignment device. The external fixation strut may provide an enhanced range of adjustable lengths, thereby preventing or minimizing any need to change out the external fixation strut during the use of the bone alignment device to accommodate minimum and maximum working ranges of the bone alignment device specified by a prescription or treatment plan. The external fixation strut may maintain a single measurement scale for a user to make length adjustments to the external fixation strut in a more reliable manner.

In one embodiment, the external fixation strut may include a main body, a threaded rod, an actuator, a first or fixed arm, coupler, component, or the like (used interchangeably herein without the intent to limit), and a second or moving arm, coupler, component, or the like (used interchangeably herein without the intent to limit). The threaded rod may be non-threadably coupled to the fixed arm and threadably coupled to the moving arm so that rotation of the threaded rod moves the moving arm relative to the fixed arm.

For example, in one embodiment, the threaded rod may be positioned within an opening of the main body. The threaded rod may be positioned through an unthreaded hole of the fixed arm. The fixed arm may be immovably fixed to a first end of the main body. The threaded rod may be positioned through a threaded hole of the moving arm. An end of the threaded rod may be fixed within a hole of the actuator. In one embodiment, the hole formed in the actuator may be threaded for threadably engaging the threaded rod. Alternatively, it is envisioned that the threaded rod may be fixed to the actuator by any now known or hereafter developed mechanism so long as rotation of the actuator causes the threaded rod to rotate such as, for example, via pins, etc.

The actuator may be positioned at a second end of the main body. The fixed arm and the moving arm may be positioned around the main body. The fixed arm and the moving arm may be connected to first and second rings or bases of a bone alignment device, respectively. The actuator may be rotated to cause the threaded rod to rotate, thereby resulting in the moving arm moving along a length of the main body. In this manner, a spacing between the rings or bases of the bone alignment device may be adjusted as the distance between the fixed arm and the moving arm is adjusted.

In one embodiment, the main body may include a single measurement scale to measure a distance between the fixed arm and the moving arm.

In one embodiment, the actuator may include a locking mechanism that prevents rotation of the actuator and the threaded rod, thereby preventing movement of the moving arm along the main body.

In one embodiment, the present disclosure is directed to an external fixation strut for use with an external fixation system. In one embodiment, the external fixation strut comprises a main body including an interior cavity, a threaded rod at least partially positioned within the interior cavity of the main body, an actuator operatively coupled to the threaded rod so that, in use, rotation of the actuator causes the threaded rod to rotate, a first fixed arm immovably coupled to the main body, and a second movable arm threadably coupled to the threaded rod so that, in use, rotation of the threaded rod causes the second movable arm to move relative to the first fixed arm.

In one embodiment, the first fixed arm is immovably coupled adjacent to a first end of the main body and the actuator is positioned adjacent to a second end of the main body.

In one embodiment, the first fixed arm includes a non-threaded opening formed therein, the non-threaded opening being arranged and configured to enable the threaded rod to pass therethrough so that, in use, rotation of the threaded rod does not cause the first fixed arm to move. The second movable arm includes a threaded opening formed therein, the threaded opening being arranged and configured to threadably couple to the threaded rod so that rotation of the threaded rod causes the second movable arm to move relative to the threaded rod and to the first fixed arm.

In one embodiment, the actuator is coupled to a first end of the threaded rod.

In one embodiment, the strut further comprises a pin for coupling the actuator to the threaded rod, the pin being arranged and configured to pass through an opening formed in the actuator and the threaded rod.

In one embodiment, the threaded rod includes a base portion formed at a second end thereof, the base portion being positioned adjacent to a first end of the main body when the threaded rod is positioned within the interior cavity of the main body.

In one embodiment, the first end of the threaded rod opposite to the base portion is arranged and configured to extend beyond a second end of the main body when the base portion is adjacent to the first end of the main body, the actuator being arranged and configured to threadably engage the first end of the threaded rod extending beyond the second end of the main body.

In one embodiment, the first fixed arm and the second movable arm are each arranged and configured to be positioned about the main body.

In one embodiment, the first fixed arm and the second movable arm each include an opening formed therein for receiving and enabling a portion of the main body to pass therethrough.

In one embodiment, the external fixation strut includes a single measurement scale to measure a distance between the first fixed arm and the second movable arm.

In one embodiment, the measurement scale is positioned on an outer surface of the main body along a length of the main body.

In one embodiment, the measurement scale is laser etched into the outer surface of the main body.

In one embodiment, the second movable arm includes a window arranged and configured to display the measurement scale so that, in use, a user can view the measurement scale when the second movable arm is positioned over the measurement scale.

In one embodiment, the second movable arm is arranged and configured to move relative to the first fixed arm between a maximum length position and a minimum length position, in the minimum length position, the second movable arm is arranged and configured to contact the first fixed arm.

In one embodiment, each of the first fixed arm and the second movable arm includes a relatively planar surface so that, in the minimum length position, the planar surface of the second movable arm directly contacts the planar surface of the first fixed arm.

In one embodiment, the main body includes first and second elongated slots extending along a longitudinal length thereof, the first and second elongated slots being arranged and configured to enable portions of the first fixed arm and the second movable arm to pass through the main body.

In one embodiment, the main body includes an end component, a first body component, and a second body component, the first and second body components coupled to and extending from the end component, the first body component occupying a first portion of an internal perimeter of the end component, the second body component occupying a second, non-overlapping portion of the internal perimeter of the end component, the first and second body components being spaced apart such that a gap is formed on either side of the second body component adjacent to the first body component.

In one embodiment, the second movable arm includes a first coupling component, a second coupling component, a first gap positioned between the first and second coupling components, and a second gap; wherein the first gap is arranged and configured to enable the first body component to pass therethrough and the second gap is arranged and configured to enable the second body component to pass therethrough so that when the second movable arm is coupled to the main body, the first coupling component is arranged and configured to be positioned about an outer surface of the main body and the second coupling component is arranged and configured to be positioned within the interior cavity of the main body.

In one embodiment, the second coupling component includes a threaded hole for threadably coupling to the threaded rod.

In one embodiment, the first fixed arm includes a first coupling component, a second coupling component, a first gap positioned between the first and second coupling components, and a second gap; wherein the first gap is arranged and configured to enable the first body component to pass therethrough and the second gap is arranged and configured to enable the second body component to pass therethrough so that when the first fixed arm is coupled to the main body, the first coupling component is arranged and configured to be positioned about an outer surface of the main body and the second coupling component is arranged and configured to be positioned within the interior cavity of the main body.

In one embodiment, the second coupling component of the first fixed arm includes a non-threaded hole for enabling the threaded rod to freely pass therethrough.

In one embodiment, the actuator includes a threaded hole for receiving an end of the threaded rod to threadably couple the threaded rod to the actuator so that rotation of the actuator rotates the threaded rod and hence moves the second movable arm relative to the first fixed arm.

In one embodiment, the strut further comprises a locking mechanism operatively associated with the actuator, the locking mechanism being arranged and configured to prevent rotation of the actuator and hence the threaded rod, thereby preventing movement of the second movable arm relative to the first fixed arm.

In one embodiment, the locking mechanism is movably positioned between a first locked position and a second unlocked position, wherein, in the first locked position, the actuator is prohibited from rotating relative to the main body, and, in the second unlocked position, the actuator is freely rotatable relative to the main body.

In one embodiment, the locking mechanism includes a pivotable lever arm, the pivotable lever arm being arranged and configured to be positioned within a cavity formed in the actuator, in use, in the first locked position the lever arm is arranged and configured to prevent rotation of the actuator relative to the main body and in the second unlocked position, the lever arm is arranged and configured to enable the actuator to freely rotate.

In one embodiment, the locking mechanism is biased to the first locked position.

In one embodiment, each of the first fixed arm and the second movable arm includes a connector for coupling to first and second rings or bases, respectively, of an external fixation system.

In one embodiment, the connector is a ball joint at an end of the first fixed arm and the second movable arm, respectively.

In one embodiment, the connector is a universal joint at an end of the first fixed arm and the second movable arm, respectively.

In one embodiment, the connector is an opening for receiving a fastener for coupling to first and second rings or bases, respectively, each of the openings being surrounded by a plurality of raised cleats to fix an axial rotation of the first and second arms relative to the first and second rings or bases, respectively.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
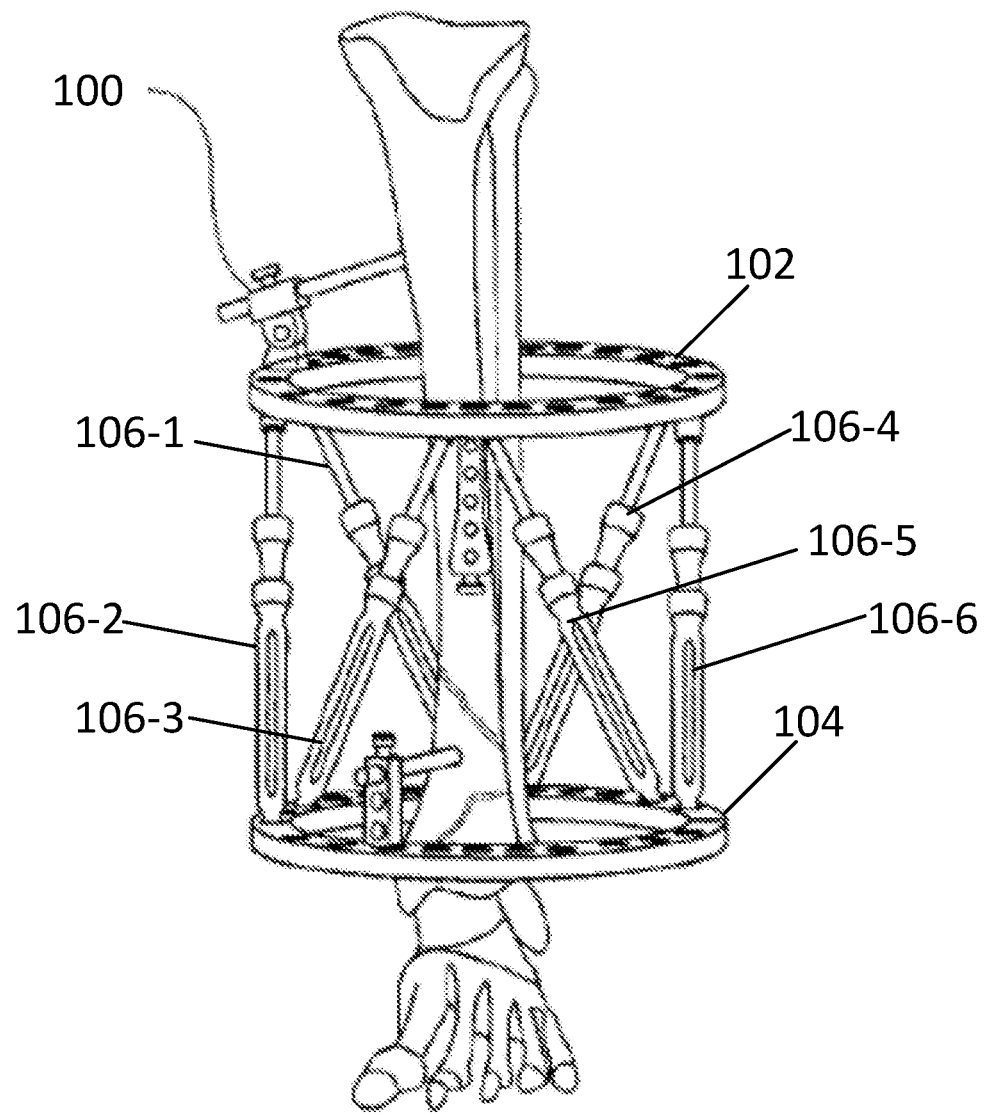
FIG. 1 illustrates an embodiment of a bone alignment device.

The drawings are not necessarily to scale. The drawings are merely representations, not intended to portray specific parameters of the disclosure. The drawings are intended to depict various embodiments of the disclosure, and therefore are not to be considered as limiting in scope. In the drawings, like numbering represents like elements.

DETAILED DESCRIPTION

An external fixation strut is provided along with systems that may include the external fixation strut as well as corresponding methods of use. The external fixation strut may provide an increased or enhanced range of adjustable lengths, thereby enabling a bone alignment device to which it may be connected to be used over a larger workable range. As a result, treatment is simplified for the patient and surgeon as the need to switch out the external fixation strut may be prevented. The external fixation strut may also include a single measurement scale that may be easily viewed and used to adjust the length of the external fixation strut, thereby ensuring more accurate length adjustments.

FIG. 1 illustrates an embodiment of a bone alignment device 100. The bone alignment device 100 may be an external fixator. As shown in FIG. 1, the bone alignment device 100 may form a hexapod having a circular, metal frame with a first ring 102 and a second ring 104 connected by six telescopic struts 106 (labeled as struts 106-1 through 106-6 in FIG. 1). Each strut 106 may be independently lengthened or shortened relative to the rest of the frame, thereby allowing for six different axes of movement.

In one embodiment, each strut 106 may include an outer body and an inner rod (e.g., a threaded rod). The outer body may be coupled to one of the rings (e.g., the second ring 104 by way of a joint). The inner rod may be coupled to the other ring (e.g., the first ring 102 by way of a joint). To lengthen or shorten one of struts 106, the outer body and the inner rod may be moved or translated relative to one another.

The bone alignment device 100 may be used to treat a variety of skeletal fractures of a patient. Typically, the bone alignment device 100 is positioned around the patient and is used to align two or more bones or pieces of bone. To do so, the length of each strut 106 may be incrementally adjusted (e.g., shortened or lengthened) in accordance with a prescription that specifies adjustments to be made to each strut 106 over time to ensure successful bone alignment. In many instances, the length of each strut 106 should be adjusted daily to comply with the provided prescription. Adjusting the length of each strut 106 adjusts the distance between the first and second rings 102 and 104. Accordingly, the maximum and minimum distances between the first and second rings 102 and 104 are determined by the maximum and minimum lengths of the struts 106, respectively.

Often, the prescription may require the first and second rings 102 and 104 to be spaced very close together and also spaced very far apart for different periods of time. That is, for example, often the prescription may require the first and second rings 102 and 104 to be spaced very close together initially, and then over time, through lengthening of the struts, the first and second rings 102 and 104 may be spaced father apart. Alternatively, for example, the prescription may require the first and second rings 102 and 104 to be spaced very far apart initially, and then over time, through shortening of the struts, the first and second rings 102 and 104 may be spaced closer together. In either event, many struts 106 may not be capable of adjustments to meet the minimum and maximum distance requirements between the first and second rings 102 and 104. As a result, the struts 106 may be required to be replaced or exchanged during the period of time a patient uses the bone alignment device 100. For example, a first set of struts 106 having a first maximum and minimum adjustable length may be attached to the first and second rings 102 and 104 for a first period of time and a second set of struts 106 having a second maximum and minimum adjustable length may be attached to the first and second rings 102 and 104 for a second, subsequent period of time. Replacing the struts 106 while the bone alignment device 100 is coupled to the patient may be complicated and uncomfortable to the patient.

To avoid replacing the struts 106, many different strut designs have been proposed. However, many of the alternative strut designs suffer from one or more drawbacks. For example, one known strut design requires multiple measurement scales to accommodate telescopic components on the strut that introduce usability challenges when length adjustments are made. Another known strut design incorporates threaded rods extending beyond the rings that may cause patient discomfort. Other known strut designs are also plagued by one or more drawbacks.

As will be described herein, the features according to the present disclosure may be used with any suitable bone alignment device now known or hereafter developed. In this regard, the present disclosure should not be limited to the details of the bone alignment device disclosed and illustrated herein unless specifically claimed and that any suitable bone alignment device may be used in connection with the principles of the present disclosure.

Figure 2:
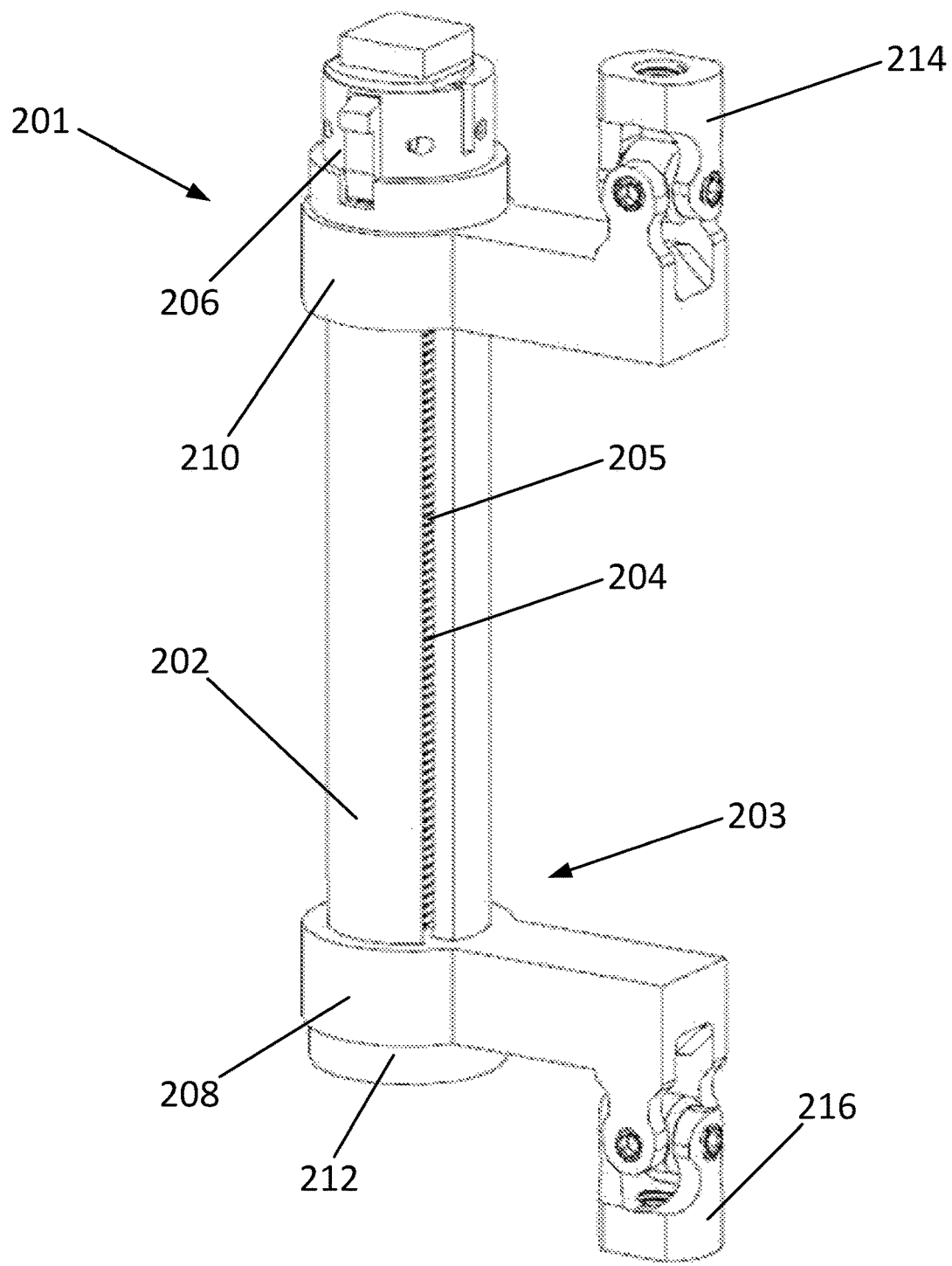
FIG. 2 illustrates a perspective view of an embodiment of an external fixation strut in accordance with one aspect of the present disclosure.

FIG. 2 illustrates an example of an embodiment of an external fixation strut 200. The external fixation strut 200 may be referred to herein as an external fixation strut without intent to limit. The external fixation strut 200 may have a length that may be adjusted to provide an increased range of motion or lengths in comparison to known fixation struts. The external fixation strut 200 may be used with or may form part of any suitable bone alignment device now known or hereafter developed. In an embodiment, the external fixation strut 200 may be coupled to first and second rings of a bone alignment device. The external fixation strut 200 may provide a range of adjustable lengths that enable a smaller minimum working distance and a larger maximum working distance between the first and second rings of a suitable bone alignment device to which the external fixation strut(s) 200 is coupled or forms a portion thereof. The external fixation strut 200 may further provide a single measurement scale, thereby improving the usability and reliability of the external fixation strut 200 as length adjustments are made.

Figure 3:
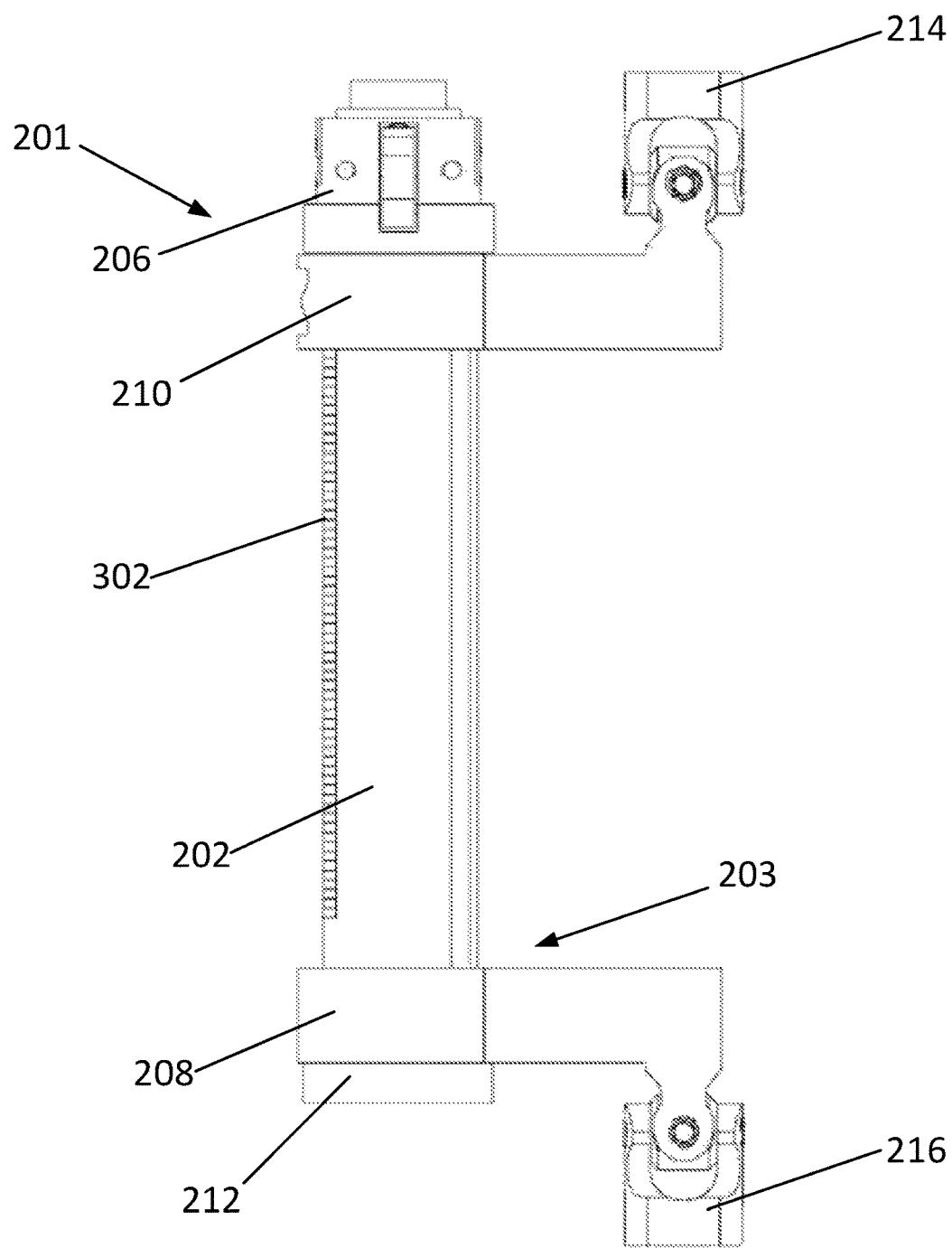
FIG. 3 illustrates a side view of the external fixation strut depicted in FIG. 2.
Figure 4:
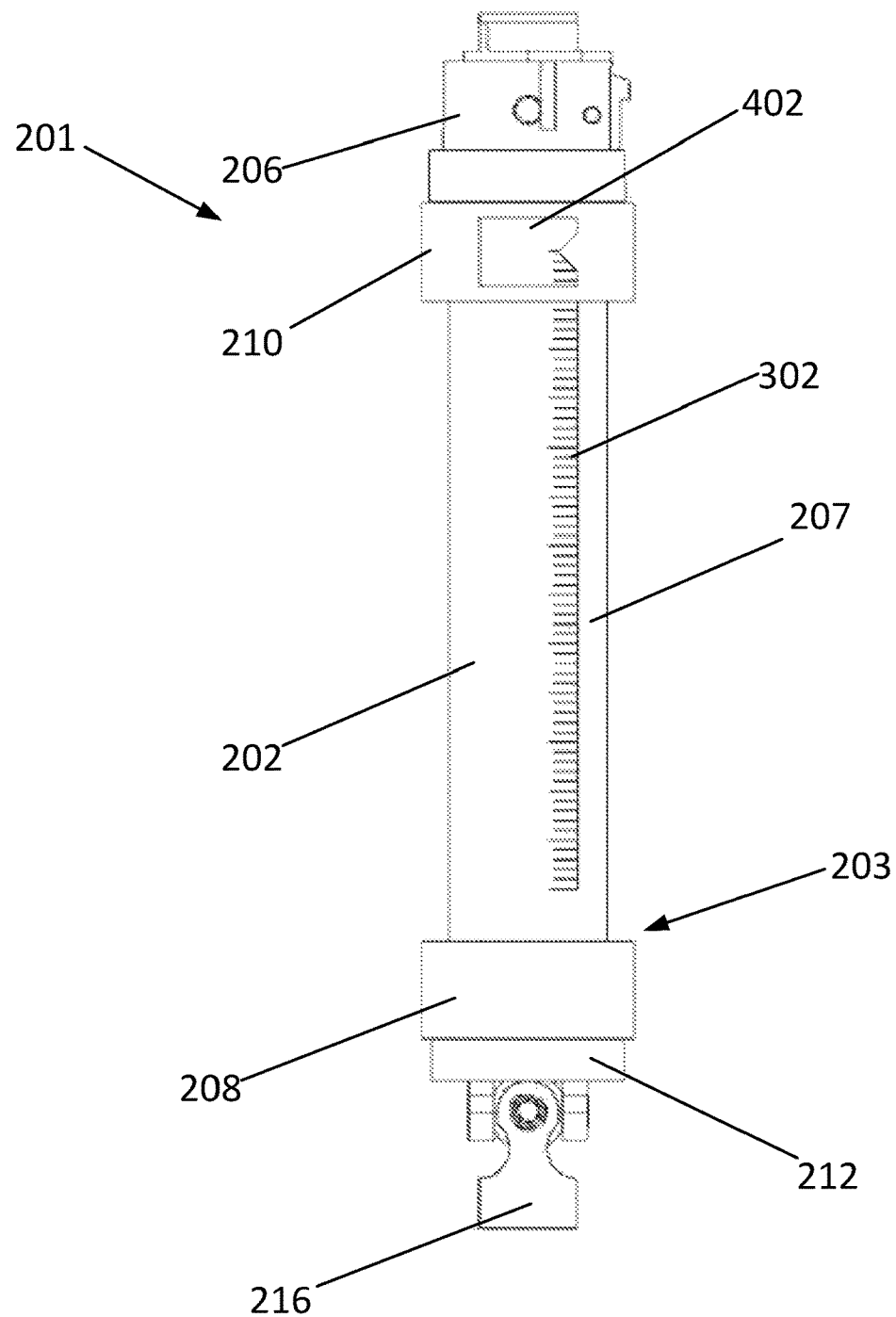
FIG. 4 illustrates a back view of the external fixation strut depicted in FIG. 2.
Figure 5:
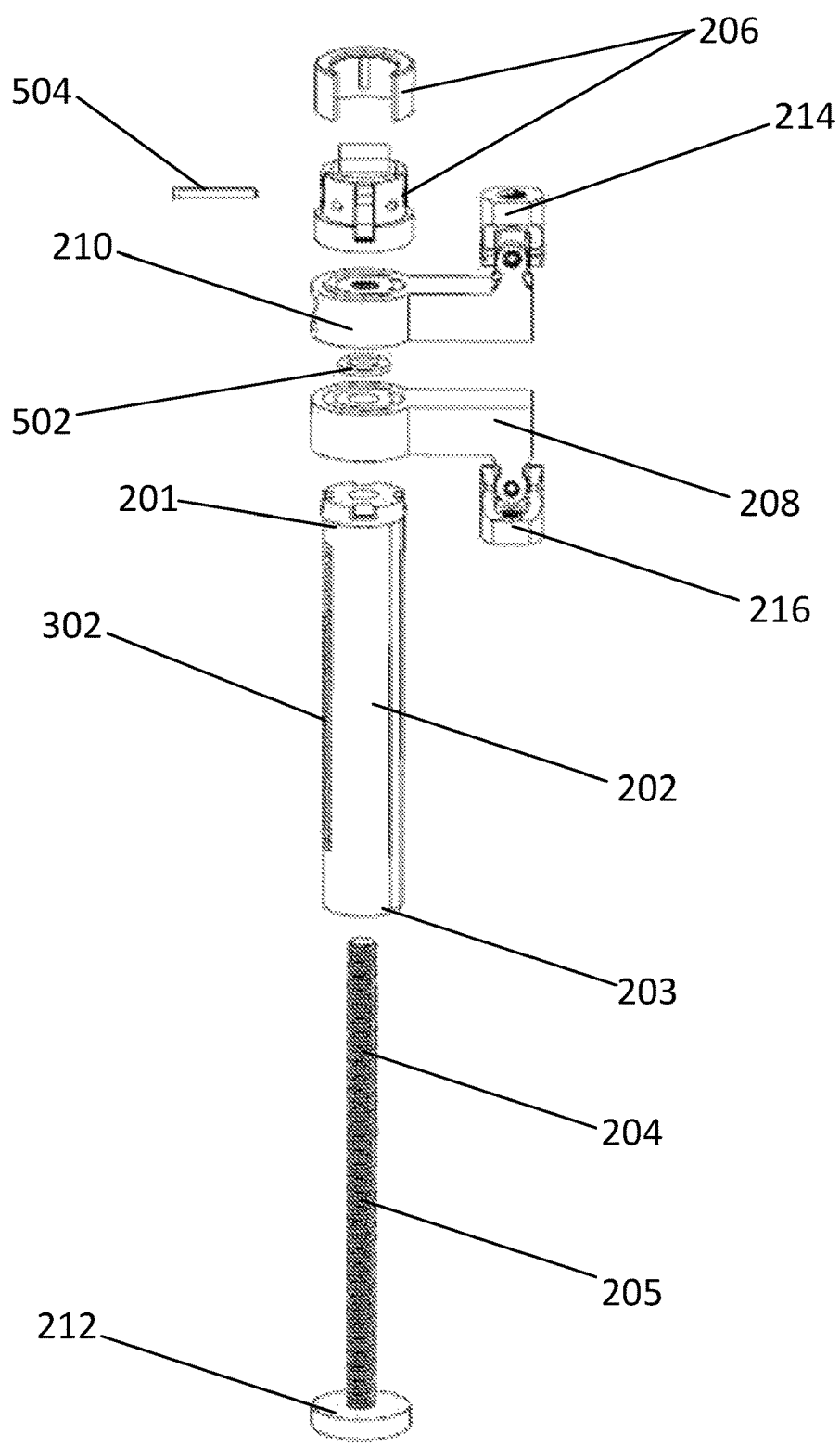
FIG. 5 illustrates a first exploded view of the external fixation strut depicted in FIG. 2.
Figure 6:
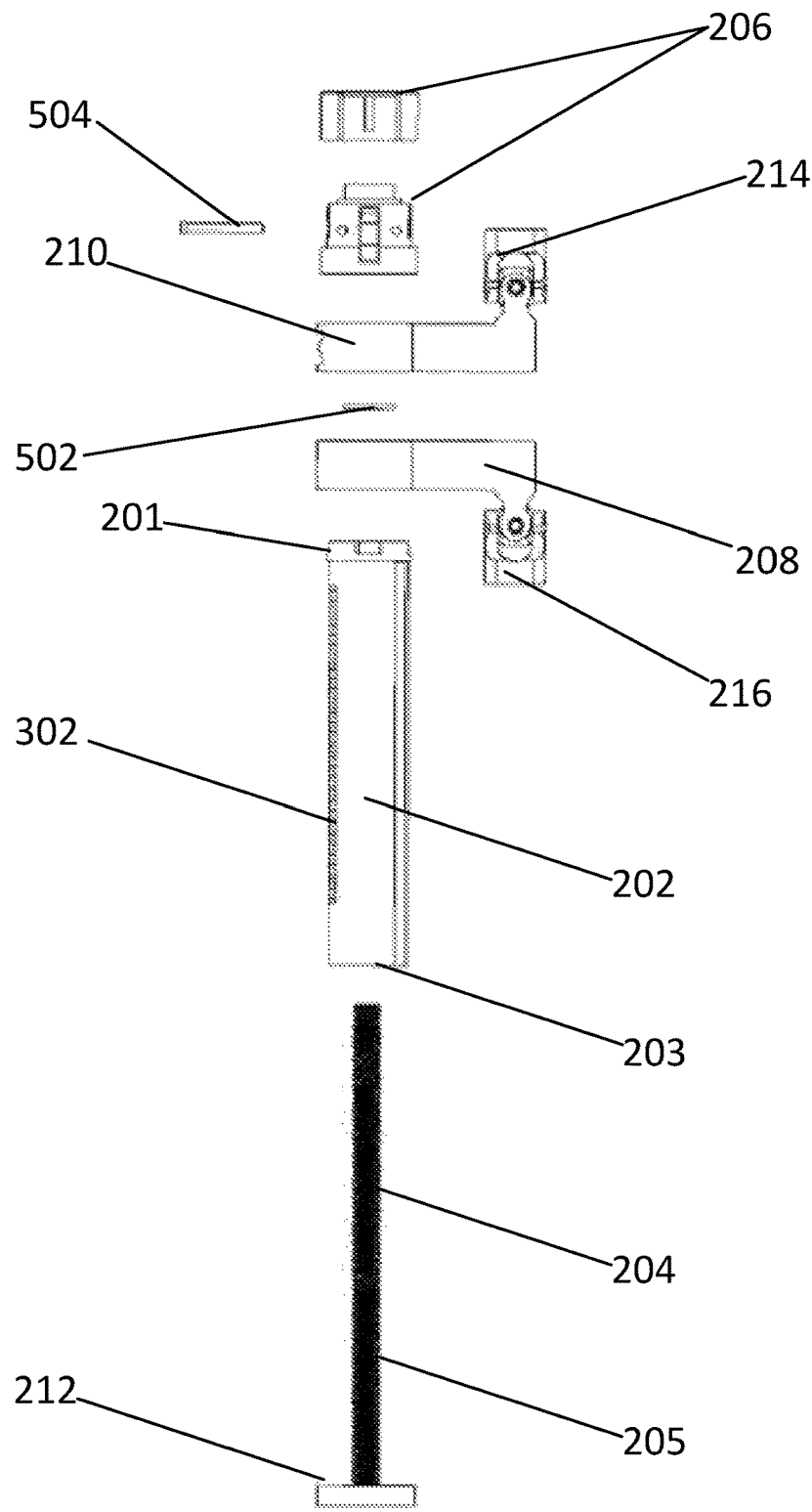
FIG. 6 illustrates a second exploded view of the external fixation strut depicted in FIG. 2.

FIG. 2 illustrates a perspective view of the external fixation strut 200. FIG. 3 illustrates a side view of the external fixation strut 200. FIG. 4 illustrates a back view of the eternal fixation strut 200. FIG. 5 illustrates a first exploded view of the external fixation strut 200. FIG. 6 illustrates a second exploded view of the external fixation strut 200.

Referring to FIGS. 2-6, the external fixation strut 200 may include a main body 202, a threaded rod 204, an actuator 206, a fixed arm 208, and a moving arm 210. The fixed arm 208 may be coupled to a first base or ring of a bone alignment device. The moving arm 210 may be coupled to a second base or ring of the bone alignment device. The fixed arm 208 may be immovably fixed or fitted to the main body 202. The moving arm 210 may be positioned within and around the main body 202. The moving arm 210 may be constrained from rotating about the main body 202 but may be moved along a length of the main body 202 so that the moving arm 210 is movable relative to the fixed arm 208.

The threaded rod 204 may have an extended threaded portion 205 and a base 212. The threaded rod 204 may be positioned within an opening, hole, interior cavity, or the like of the main body 202 such that the base 212 is positioned adjacent to a first end 203 of the main body 202. The fixed arm 208 may include a hole or opening 2012 (see FIG. 20) that allows the threaded rod 204 to pass through unhindered. The moving arm 210 and the actuator 206 may each have a threaded opening or hole 1712 and 2502, respectively (see FIGS. 17 and 18) for threadably receiving the threaded rod 204.

The threaded portion 205 of the threaded rod 204 may be inserted through the hole formed in the fixed arm 208 and into the interior cavity of the main body 202. The threaded rod portion of the threaded rod 204 may be threaded through the hole formed in the moving arm 210. A portion of the threaded rod 204 may extend out beyond the main body 202 when the base 212 is adjacent to the fixed arm 208. The actuator 206 may be fixedly threaded onto the threaded portion 205 of the threaded rod 204 at a second end 201 of the main body 202 opposite the position of the fixed arm 208.

The actuator 206 may be rotated relative to the main body 202 thereby causing the threaded rod 204 to rotate, which due to the threaded engagement with the moving arm 210 and the non-threaded engagement with the fixed arm 208 causes the moving arm 210 to move along the length of the main body 202. For example, rotating the actuator 206 in a first direction (e.g., clockwise) may cause the moving arm 210 to move toward the fixed arm 208, thereby reducing a working length of the external fixation strut 200. Rotating the actuator in a second direction (e.g., counterclockwise) may cause the moving arm 210 to move toward the actuator 206, thereby increasing a working length of the external fixation strut 200.

Referring to FIGS. 3-6, the main body 202 may include a measurement scale 302. The measurement scale 302 may be positioned on an outer surface 207 of the main body 202 along the length of the main body 202. In one embodiment, the measurement scale 302 may be laser etched into the outer surface of the main body 202. The measurement scale 302 may be used to measure an adjustable length of the external fixation strut 200—for example, a distance between the fixed arm 208 and the moving arm 210. As described herein, the external fixation strut 200 may enhance usability by providing a single measurement scale 302 in comparison to known struts that require two or more measurement scales that may be challenging and confusing to use.

Referring to FIG. 4, in one embodiment, the moving arm 210 may include an opening or window 402 that is aligned with the measurement scale 302. The opening or window 402 within the moving arm 210 may allow an individual to view the measurement scale 302 when the moving arm 210 is positioned over the measurement scale 302.

In use, and as previously mentioned, the external fixation strut 200 and specifically, the moving and fixed arms 210, 208 may be coupled to a ring or base of a bone alignment device. The fixed arm 208 and the moving arm 210 may each include any type of suitable connector or joint now known or hereafter developed to facilitate coupling to a ring or base of a bone alignment device. The connector of the fixed arm 208 may allow the fixed arm 208 to be coupled to a first ring of a bone alignment device. The connector of the moving arm 210 may allow the moving arm 210 to be coupled to a second ring of a bone alignment device.

Referring to FIGS. 2-6, in one embodiment, the moving arm 210 may include or be coupled to a connector component 214 such as, for example, a universal joint and the fixed arm 208 may include or be coupled to a connector component 216 such as, for example, a universal joint. The universal joint may be attached or coupled to a first ring of a bone alignment device such as, for example, the first ring 102 of the bone alignment device 100. The universal joint may be attached or coupled to a second ring of a bone alignment device such as, for example, the second ring 104 of the bone alignment device 100.

Referring to FIGS. 5 and 6, in one embodiment, the external fixation strut 200 may include a washer 502. The washer 502 may be a low friction washer. The washer 502 may be positioned between the actuator 206 and the main body 202. The washer 502 may enable the actuator 206 to rotate more easily about the main body 202.

FIGS. 5 and 6 further show that in one embodiment, the external fixation strut 200 may include a pin 504. The pin 504 may couple the actuator 206 to the threaded rod portion of the threaded rod 204 and/or may couple together one or more components of the actuator 206. As an example, the pin 504 may be positioned within one or more holes or openings formed in the actuator 206 and through a corresponding and aligned hole or opening formed in the threaded rod portion of the threaded rod 204.

FIGS. 2-4 show the external fixation strut 200 in a first position. Specifically, FIGS. 2-4 show the external fixation strut 200 with the moving arm 210 positioned a maximum distance away from the fixed arm 208. Accordingly, FIGS. 2-4 show the external fixation strut 200 with a maximum adjustable length.

Figure 7:
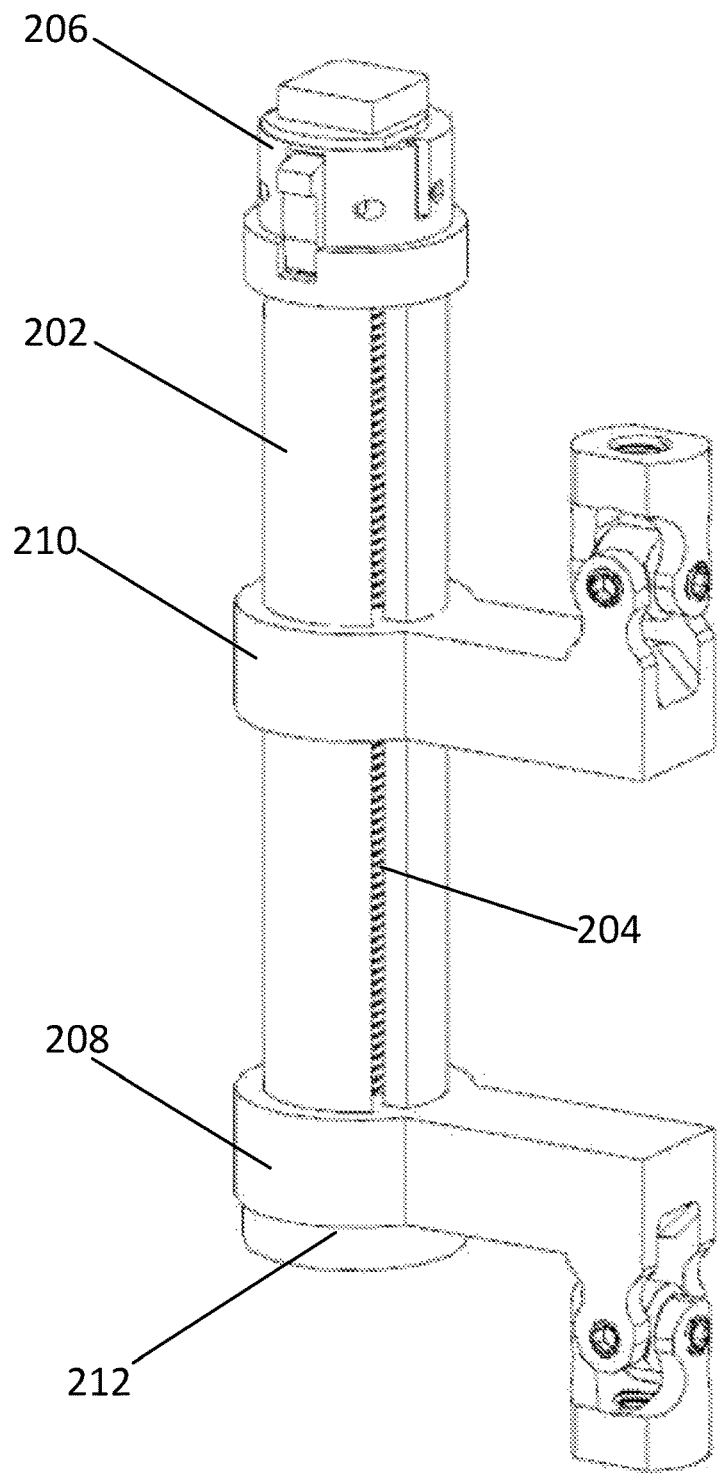
FIG. 7 illustrates a perspective view of the external fixation strut depicted in FIG. 2, the external fixation strut illustrated in an intermediate adjustable length position.

FIG. 7 shows the external fixation strut 200 in a second position. Specifically, FIG. 7 shows the external fixation strut 200 with the moving arm 210 positioned at an intermediate distance away from the fixed arm 208. Accordingly, FIG. 7 show the external fixation strut 200 having an intermediate adjustable length. FIG. 7 shows a perspective view of the external fixation strut 200 having the intermediate adjustable length.

Figure 8:
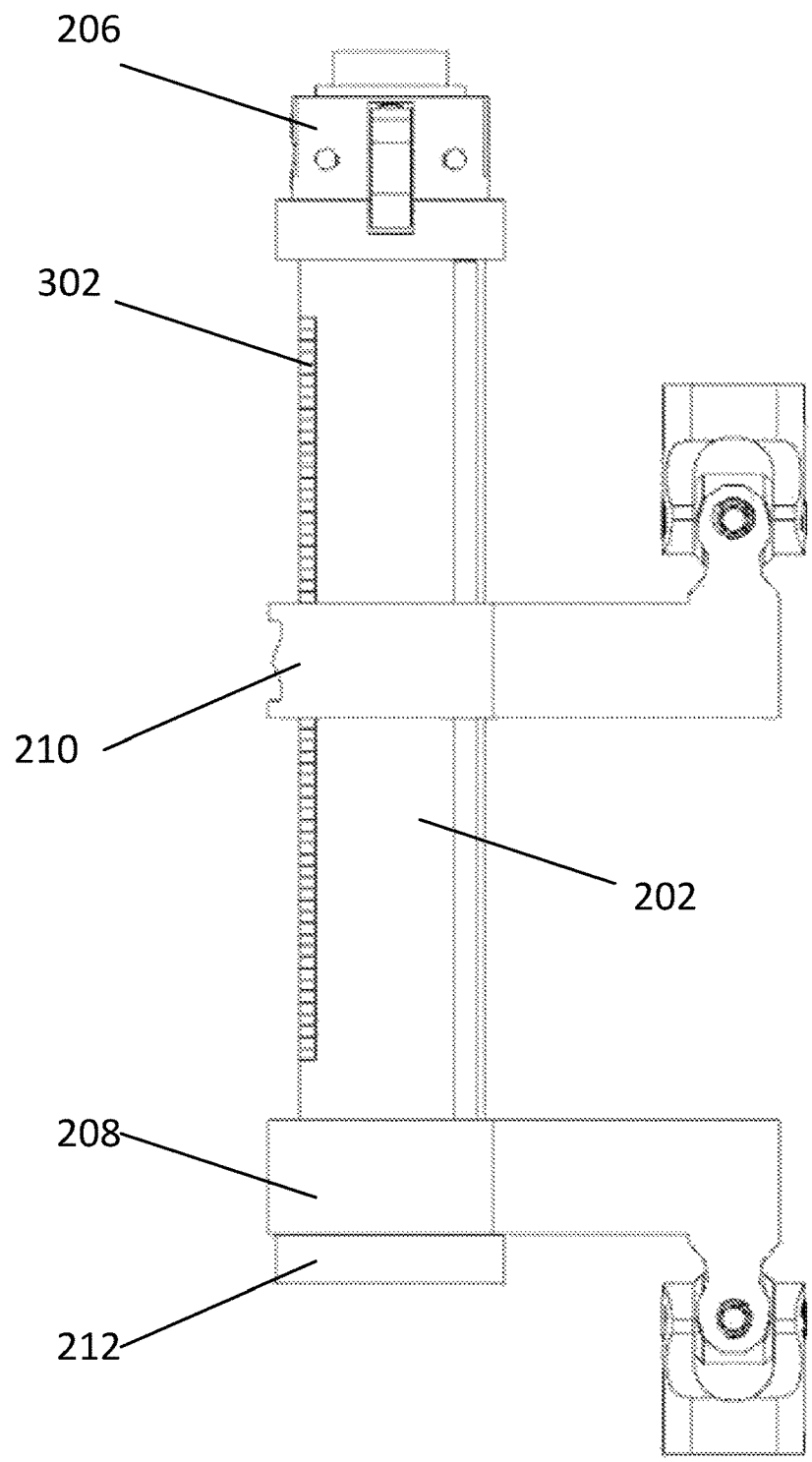
FIG. 8 illustrates a side view of the external fixation strut depicted in FIG. 2, the external fixation strut illustrated in an intermediate adjustable length position.
Figure 9:
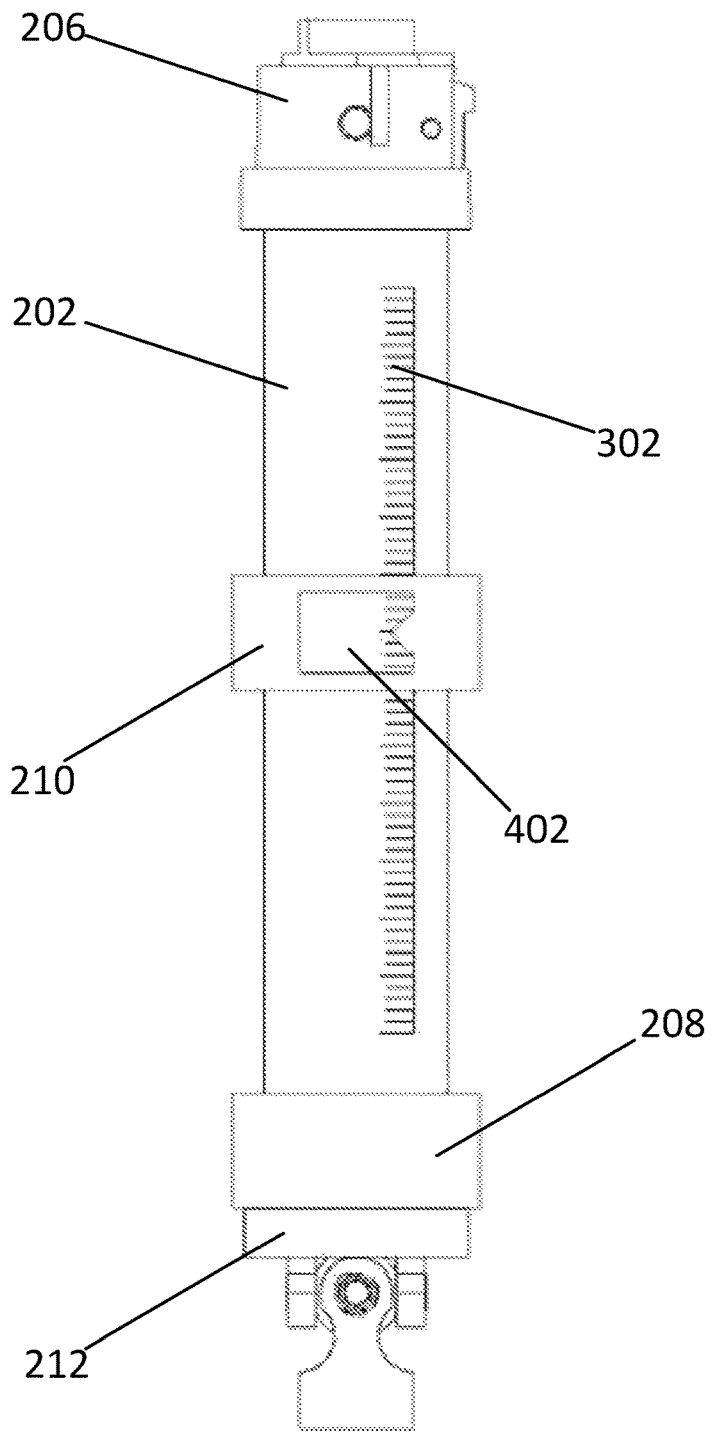
FIG. 9 illustrates a back view of the external fixation strut depicted in FIG. 2, the external fixation strut illustrated in an intermediate adjustable length position.
Figure 10:
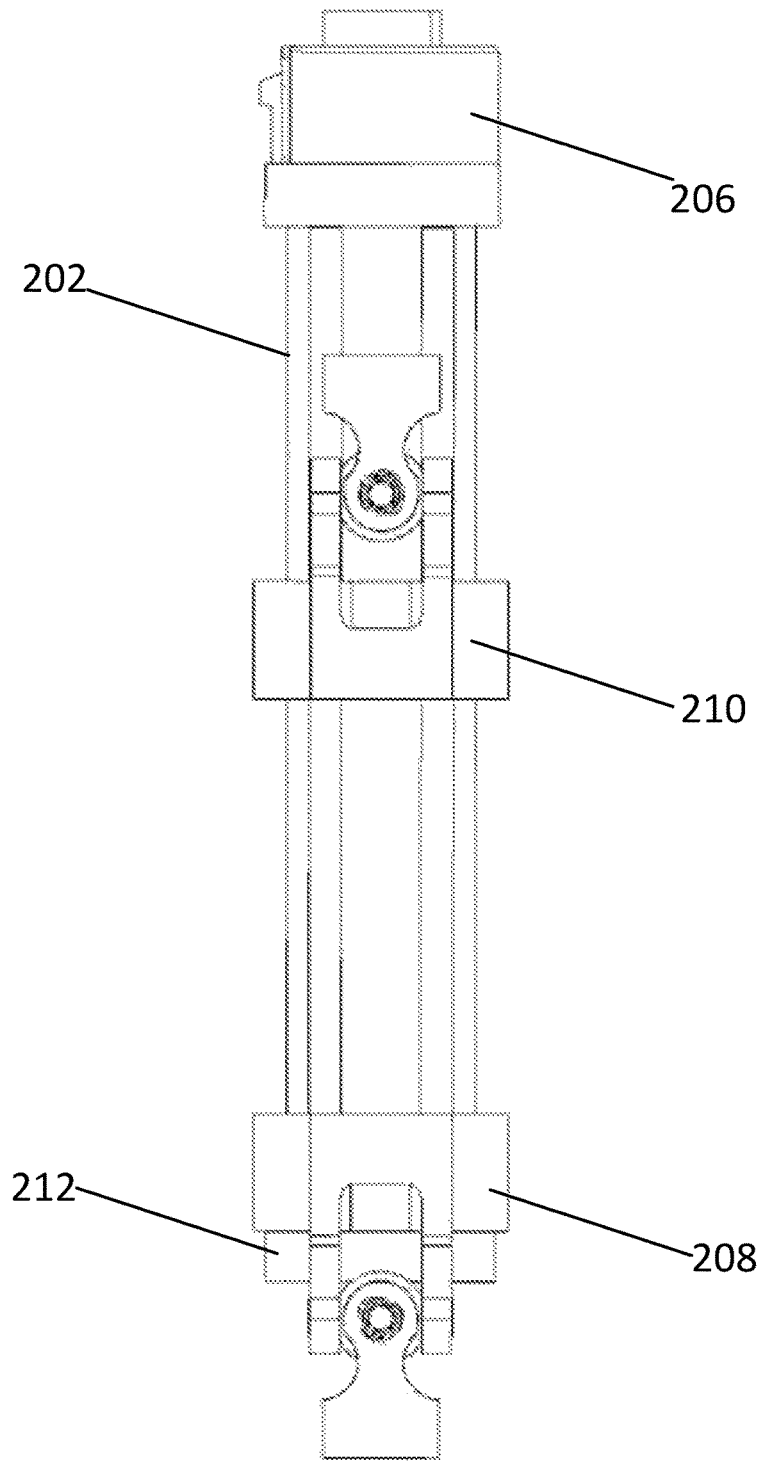
FIG. 10 illustrates a front view of the external fixation strut depicted in FIG. 2, the external fixation strut illustrated in an intermediate adjustable length position.

FIGS. 8-10 illustrate various views of the external fixation strut in an intermediate adjustable length position corresponding to the depiction of the external fixation strut 200 in FIG. 7. In particular, FIG. 8 illustrates a side view of the external fixation strut 200 corresponding to the depiction of the external fixation strut 200 in FIG. 7. FIG. 9 illustrates a back view of the external fixation strut 200 corresponding to the depiction of the external fixation strut 200 in FIG. 7. FIG. 10 illustrates a front view of the external fixation strut 200 corresponding to the depiction of the external fixation strut 200 in FIG. 7. Referring to FIGS. 7-10, the moving arm 210 is positioned on the main body 202 between the fixed arm 208 and the actuator 206.

Figure 11:
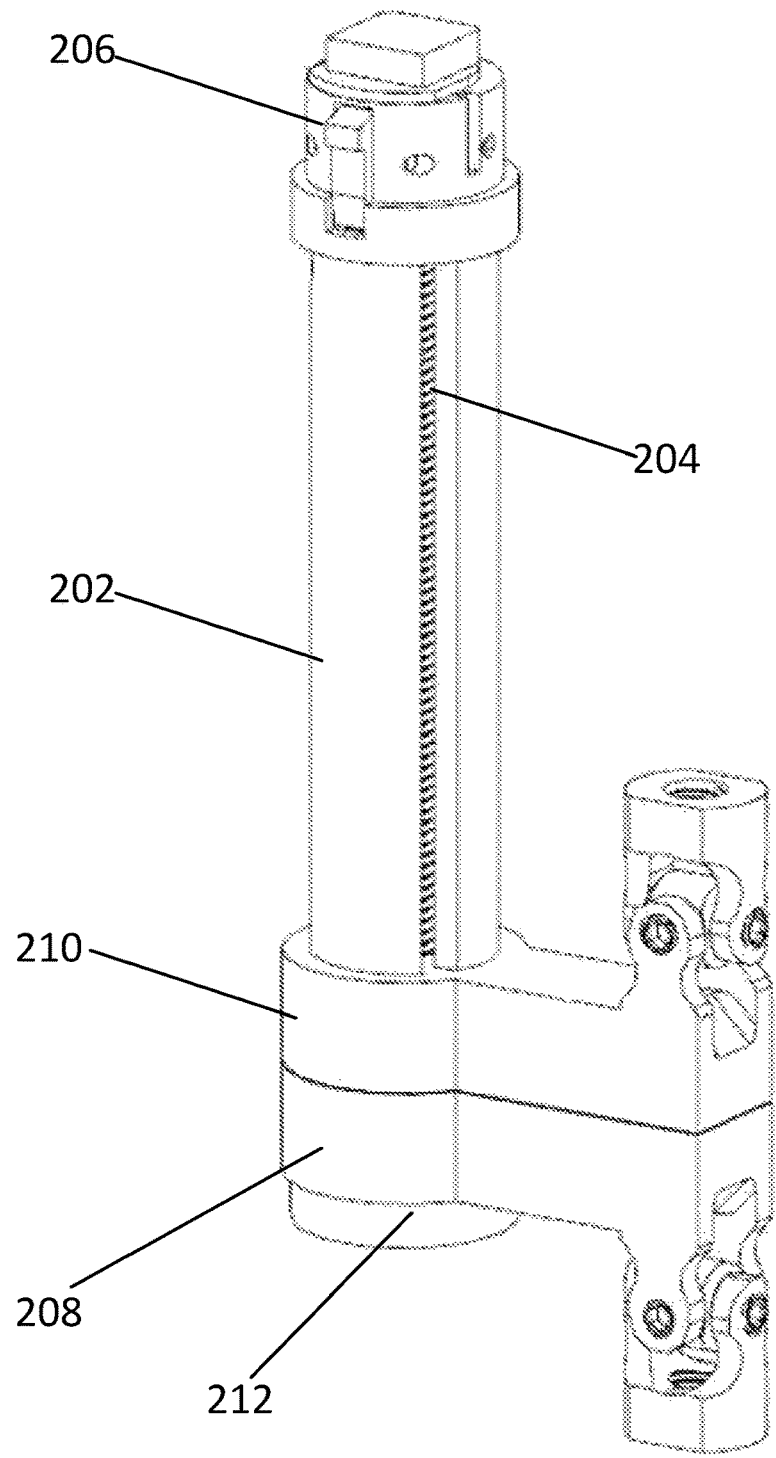
FIG. 11 illustrates a perspective view of the external fixation strut depicted in FIG. 2, the external fixation strut illustrated in a minimum adjustable length position.

FIG. 11 shows the external fixation strut 200 in a third position. Specifically, FIG. 11 shows the external fixation strut 200 with the moving arm 210 positioned a minimum distance away from the fixed arm 208. Accordingly, FIG. 11 show the external fixation strut 200 having a minimum adjustable length. FIG. 11 shows a first view of the external fixation strut 200 having the intermediate adjustable length. As shown, the moving arm 210 is adjacent to and may touch the fixed arm 208.

Figure 12:
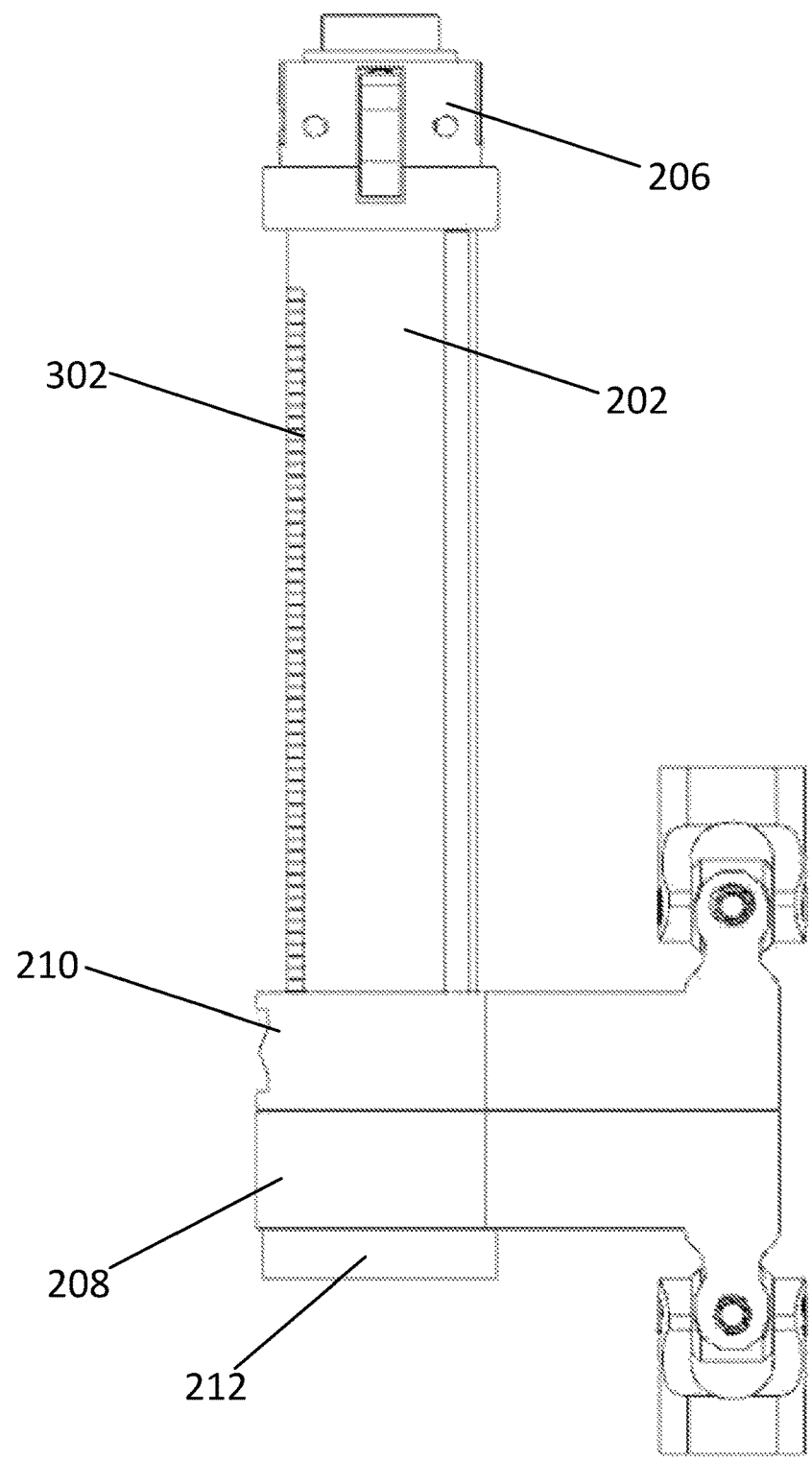
FIG. 12 illustrates a side view of the external fixation strut depicted in FIG. 2, the external fixation strut illustrated in a minimum adjustable length position.
Figure 13:
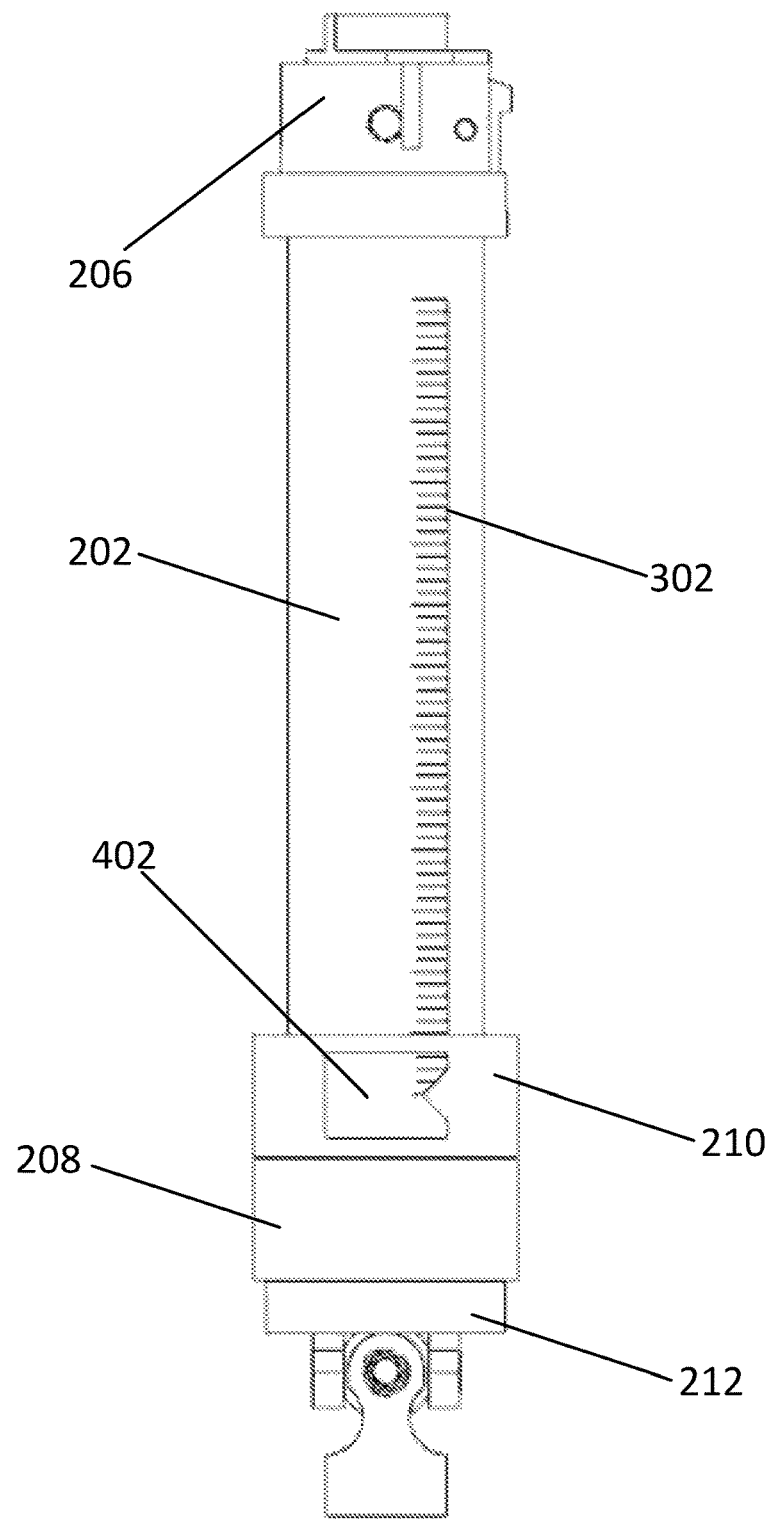
FIG. 13 illustrates a back view of the external fixation strut depicted in FIG. 2, the external fixation strut illustrated in a minimum adjustable length position.

FIGS. 12-13 illustrate various views of the external fixation strut 200 in the minimum adjustable length position corresponding to the depiction of the external fixation strut 200 in FIG. 11. In particular, FIG. 12 illustrates a side view of the external fixation strut 200 corresponding to the depiction of the external fixation strut 200 in FIG. 11. FIG. 13 illustrates a back view of the external fixation strut 200 corresponding to the depiction of the external fixation strut 200 in FIG. 11. Referring to FIGS. 11-13, the moving arm 210 is positioned on the main body 202 next to the fixed arm 208.

Referring to FIGS. 2-13, the external fixation strut 200 provides numerous advantages. The external fixation strut 200 provides an increased or larger range of adjustable lengths as compared to other known struts, thereby preventing or minimizing any need to change out the external fixation strut 200 when used with a bone alignment device. In various embodiments, the external fixation strut 200 may provide a larger working range by increasing and/or maximizing an amount of the threaded rod portion of the threaded rod 204 and the main body 202 that may be used. The external fixation strut 200 may also allow the movable arm 210 to move along the entire length of the threaded rod 204 and may be allowed to contact the fixed arm 208. In an embodiment, the fixed arm 208 and the moving arm 210 may have relatively planar corresponding surfaces so that the fixed arm 208 and the moving arm 210 may be placed into direct contact with each other as shown in FIGS. 11-13. As a result, the external fixation strut 200 may be optimized for limited spaces, thereby allowing rings or bases of a bone alignment device to be spaced closer together. As described herein, the external fixation strut 200 may be connected to a ring or base of a bone alignment device using any suitable connector and is not limited to the connections illustrated in FIGS. 2-13. Although not shown the external fixation strut 200 may also be configured such that the connectors (e.g., ring connector components, such as 214 and 216) on the fixed arm 208 and moving arm 210, are oriented between the fixed arm 208 and moving arm 210 rather than outside of the arms. Further, as will be described in greater detail below, the external fixation strut 200 may include any type of locking mechanism to prevent rotation of the actuator 206 and therefore prevent movement of the moving arm 210.

Figure 14:
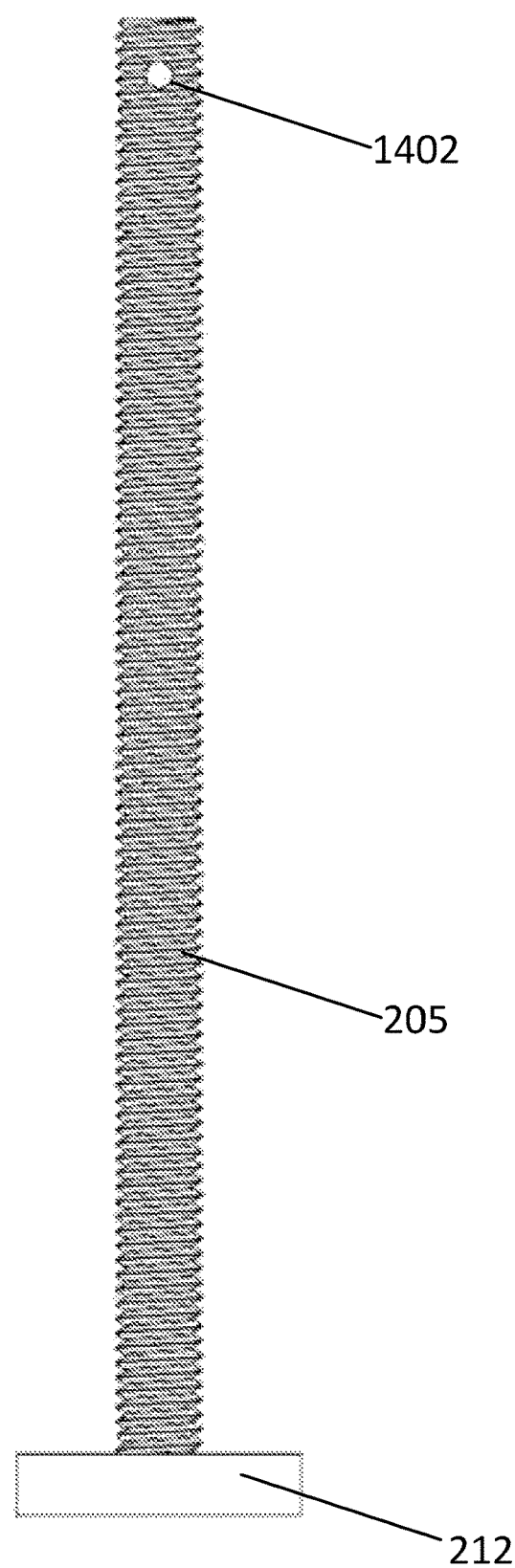
FIG. 14 illustrates an embodiment of a threaded rod of the external fixation strut depicted in FIG. 2 in accordance with one aspect of the present disclosure.

FIG. 14 illustrates an embodiment of the threaded rod 204. As shown in FIG. 14 the threaded rod 204 may include the threaded portion 205 and the base 212. In one embodiment, the threaded rod 204 may include a hole or opening 1402. The hole or opening 1402 may be used with the pin 504 depicted in FIGS. 5 and 6 to couple or connect the threaded rod 204 to the actuator 206.

Figure 15:
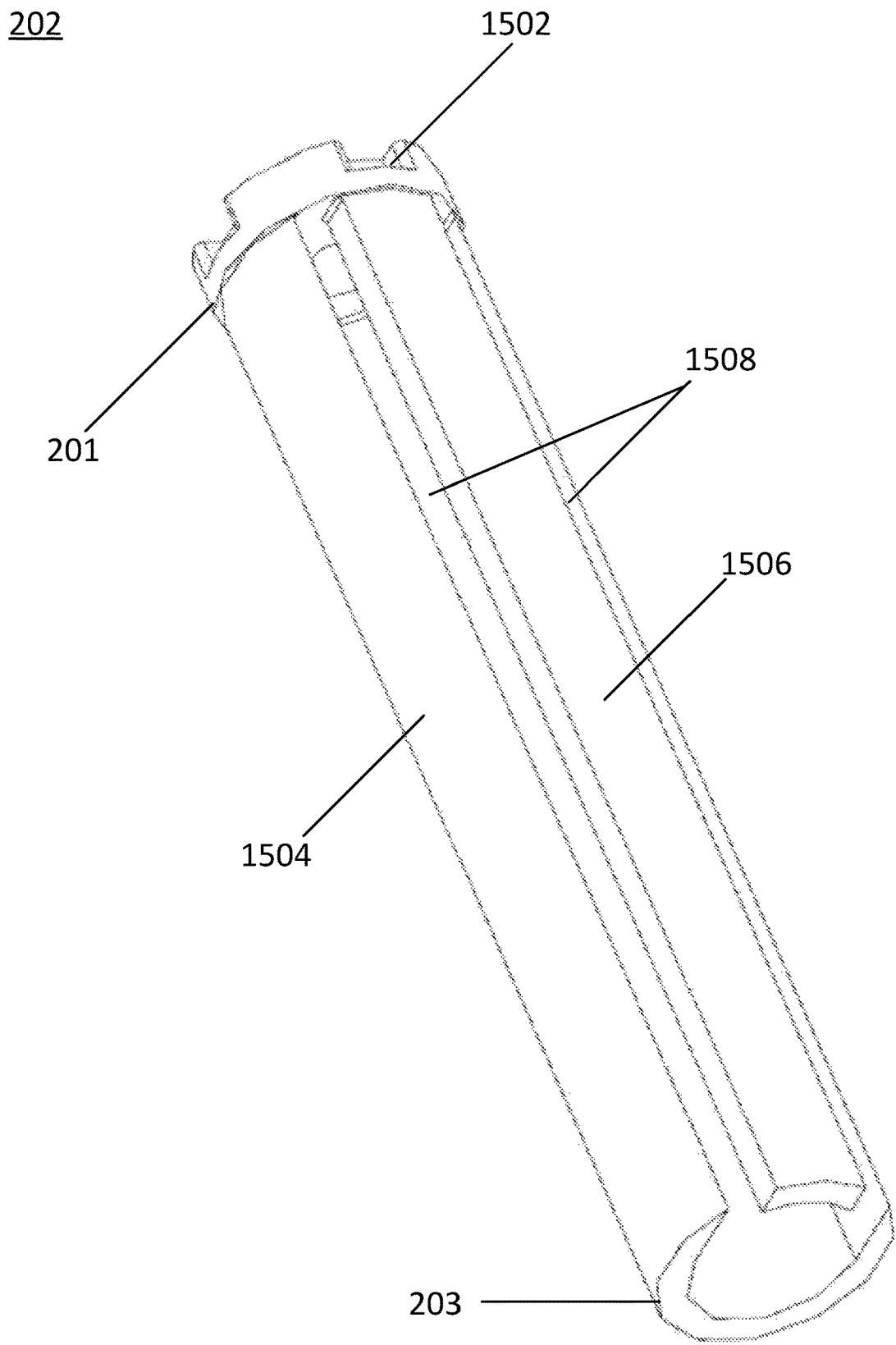
FIG. 15 illustrates a perspective view of an embodiment of a main body of the external fixation strut depicted in FIG. 2 in accordance with one aspect of the present disclosure.
Figure 16:
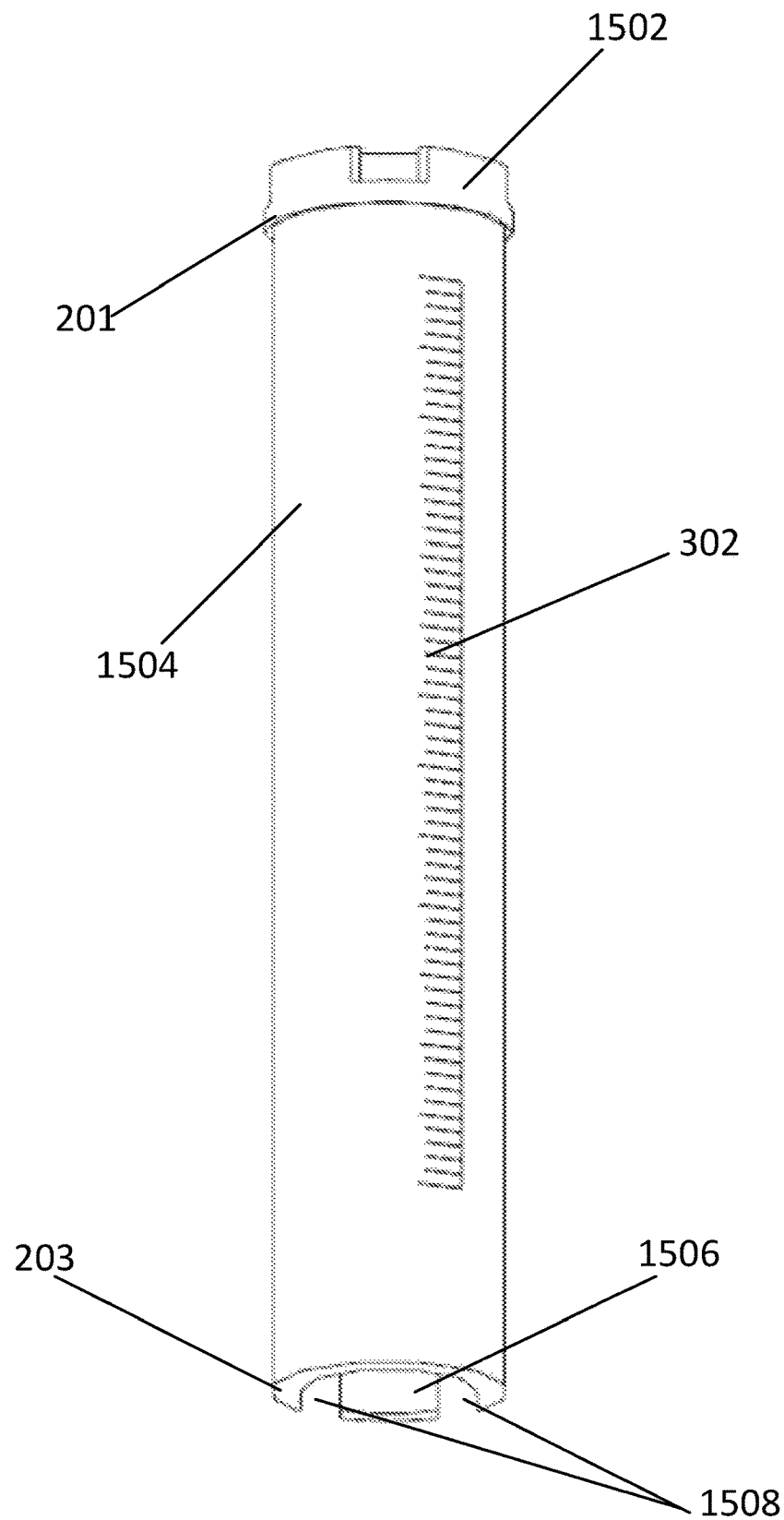
FIG. 16 illustrates an alternate perspective view of the main body depicted in FIG. 15.

FIGS. 15 and 16 illustrate an embodiment of the main body 202. Specifically, FIG. 15 illustrates a perspective view of the main body 202 and FIG. 16 illustrates an alternate perspective view of the main body 202. Referring to FIGS. 15 and 16, the main body 202 may include a top or end component 1502, a first body component 1504, and a second body component 1506. In use, the top component 1502 may be coupled or connected to the actuator 206. The first and second body components 1504 and 1506 may be connected to the top component 1502 and may extend from the top component 1502. As shown in FIGS. 15 and 16, the main body 202 may have a generally cylindrical or tubular shape, although any other suitable shape may be used. Alternatively, it should be understood that the first and second body components may be formed as an integral member with slots formed therein.

The first body component 1504 may be shaped to occupy a first portion of an internal perimeter of the top component 1502 and the second body component 1506 may be shaped to occupy a second, non-overlapping portion of an internal perimeter of the top component 1502. The first and second body components 1504 and 1506 may be spaced apart such that a gap, an opening, an elongated slot or the like 1508 (interchangeably used herein without the intent to limit) is formed on either side of the second body component 1506 adjacent to the first body component 1504. That is, as illustrated, the main body 202 may be arranged and configured to include first and second elongated slots 1508 extending along a longitudinal length thereof. As described further herein, the arrangement of the first and second body components 1504 and 1506 (e.g., incorporation of elongated slots 1508) facilitates coupling of the fixed arm 208 and the moving arm 210 with the threaded rod 204, which is positioned within the main body 202. That is, the slots, gaps, or openings enable portions of the moving arm 210 and the fixed arm 208 to pass through the main body 202, as will be described in greater detail below. FIG. 16 shows that the measurement scale 302 may be provided on the first body component 1504.

Figure 17:
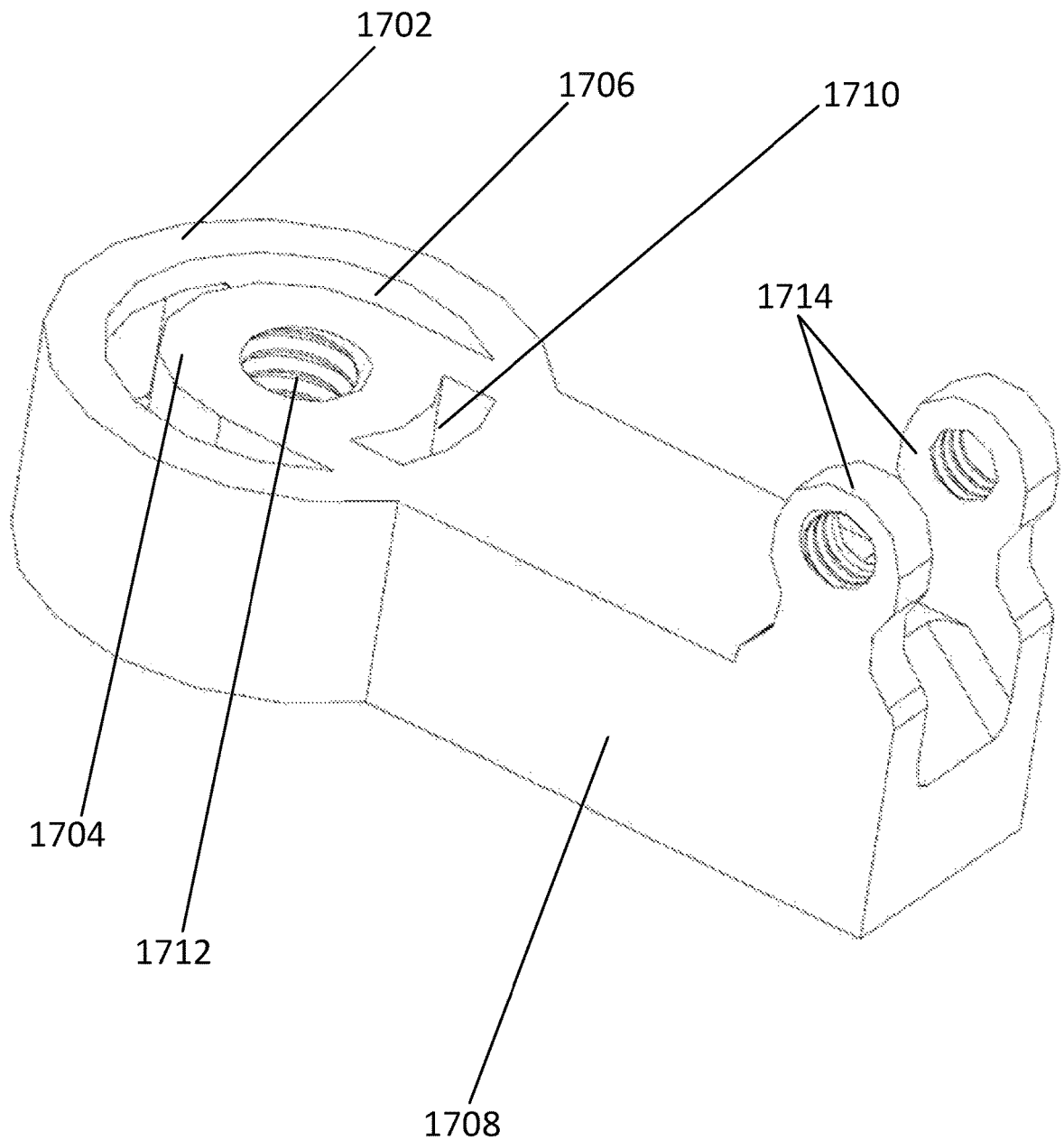
FIG. 17 illustrates a perspective view of an embodiment of a moving arm of the external fixation strut depicted in FIG. 2 in accordance with one aspect of the present disclosure.

FIG. 17 illustrates a perspective view of an embodiment of the moving arm 210. As shown, the moving arm 210 may include a first member, portion, or coupling component 1702 and a second member, portion, or coupling component 1704 (interchangeably used herein without the intent to limit). The first and second coupling components 1702 and 1704 may be separated by a first gap or opening 1706. The first and second coupling components 1702 and 1704 may be connected to an arm component 1708. The moving arm 210 may further include a second gap or opening 1710. It should be understood that the moving arm 210 may be formed by any suitable manner, for example, as an integral member with one or more openings formed therein.

In one embodiment, the first opening 1706 may be shaped and configured to receive the first body component 1504 of the main body 202 and the second opening 1710 may be shaped and configured to receive the second body component 1506 of the main body 202. Accordingly, when the moving arm 210 is connected to the main body 202, the first coupling component 1702 may be positioned on an outside of the main body 202 and the second coupling component 1704 may be positioned within an inside of the main body 202.

As further shown in FIG. 17, the second coupling component 1704 may include a threaded hole or opening 1712 for threadably coupling to the threaded portion 205 of the threaded rod 204. Accordingly, as the threaded rod 204 is rotated (e.g., by rotation of the actuator 206), the moving arm 210 may move along the main body 202.

As shown, the arm component 1708 may extend away from the first and second coupling components 1702 and 1704. The arm component 1708 may include one or more components for connecting the moving arm 210 to a ring or other component of a bone alignment device. The arm component 1708 may include any suitable type of one or more components for connecting the moving arm 210 to a ring or other component of a bone alignment device. For example, the arm component 1708 may include any combination of hinges, ball joints, universal joints, and fixed joints for connecting to a ring or other component of a bone alignment device. In one embodiment, the moving arm 210 may include connector components 214. The connector components 214 may be connected to a joint such as, for example, the universal joint, a ball-joint, or the like.

Figure 18:
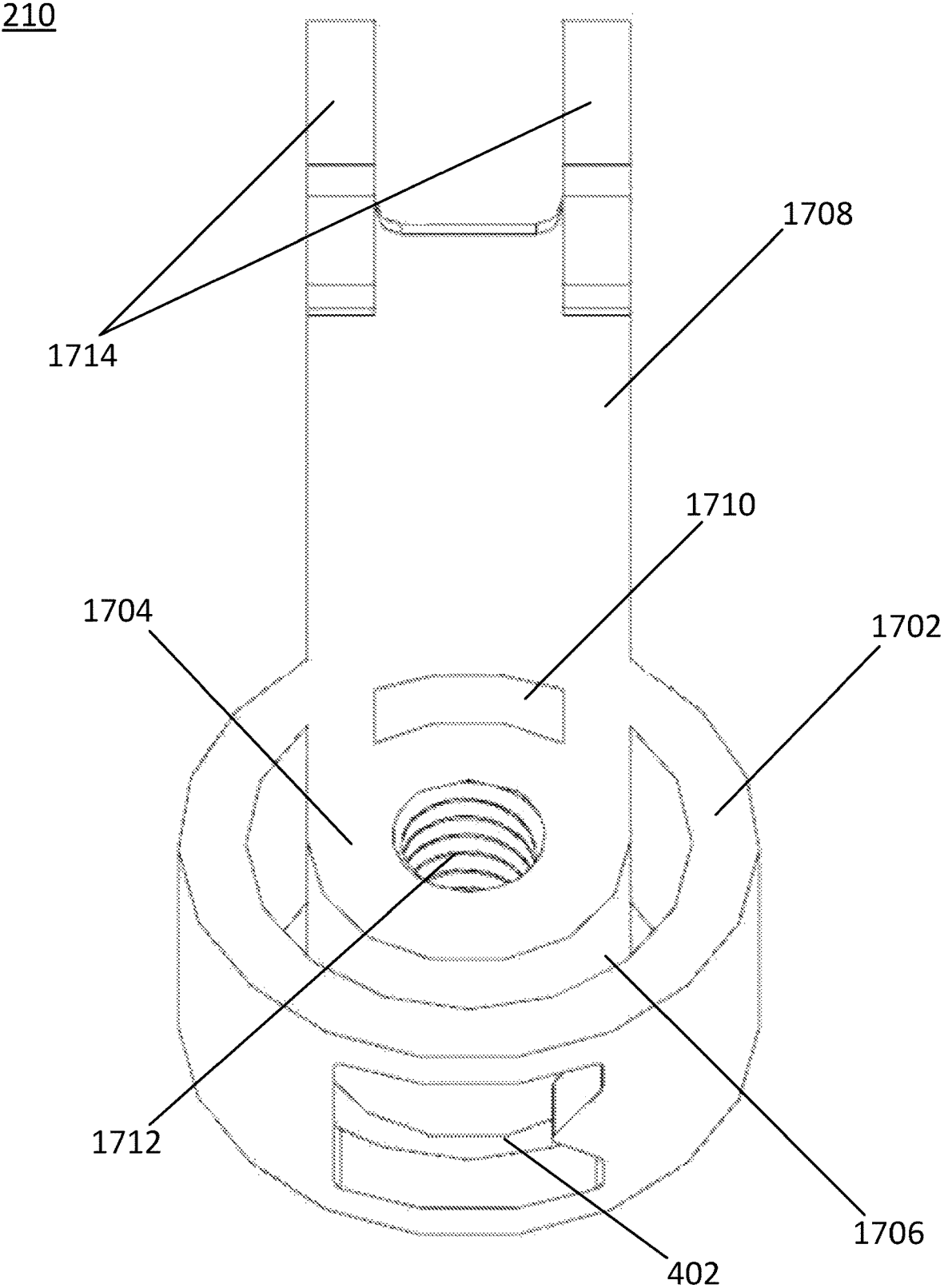
FIG. 18 illustrates an alternate perspective view of the moving arm depicted in FIG. 17.

FIG. 18 illustrates an alternate perspective view of the moving arm 210. As shown, the window 402 may be positioned through the first coupling component 1702 to allow the measurement scale 302 to be viewed when the moving arm 210 is attached to the main body 202.

Figure 19:
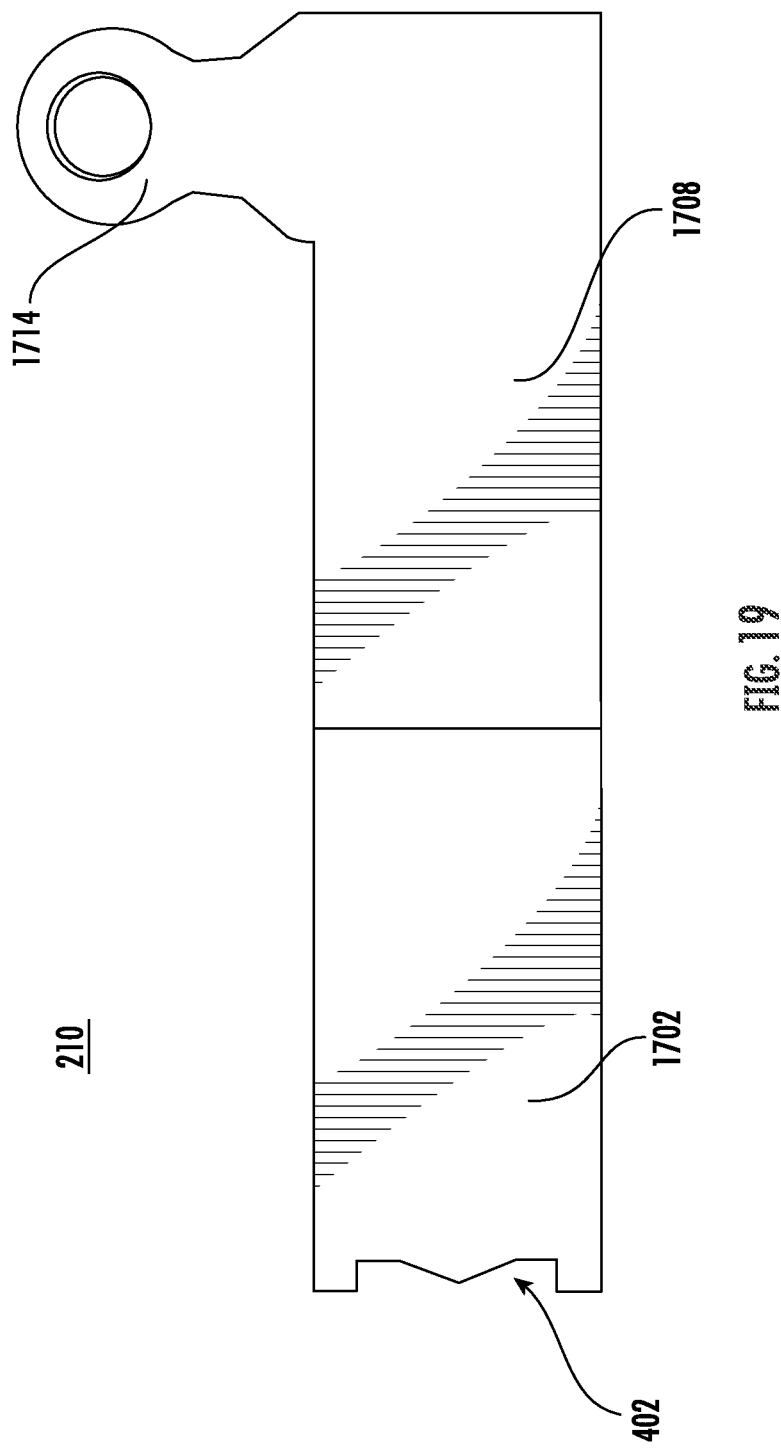
FIG. 19 illustrates a side view of the moving arm depicted in FIG. 17.

FIG. 19 illustrates a side view of the moving arm 210. FIG. 19 shows the relative arrangement of the first coupling component 1702, the arm component 1708, the connector components 1714, and the window 402.

Figure 20:
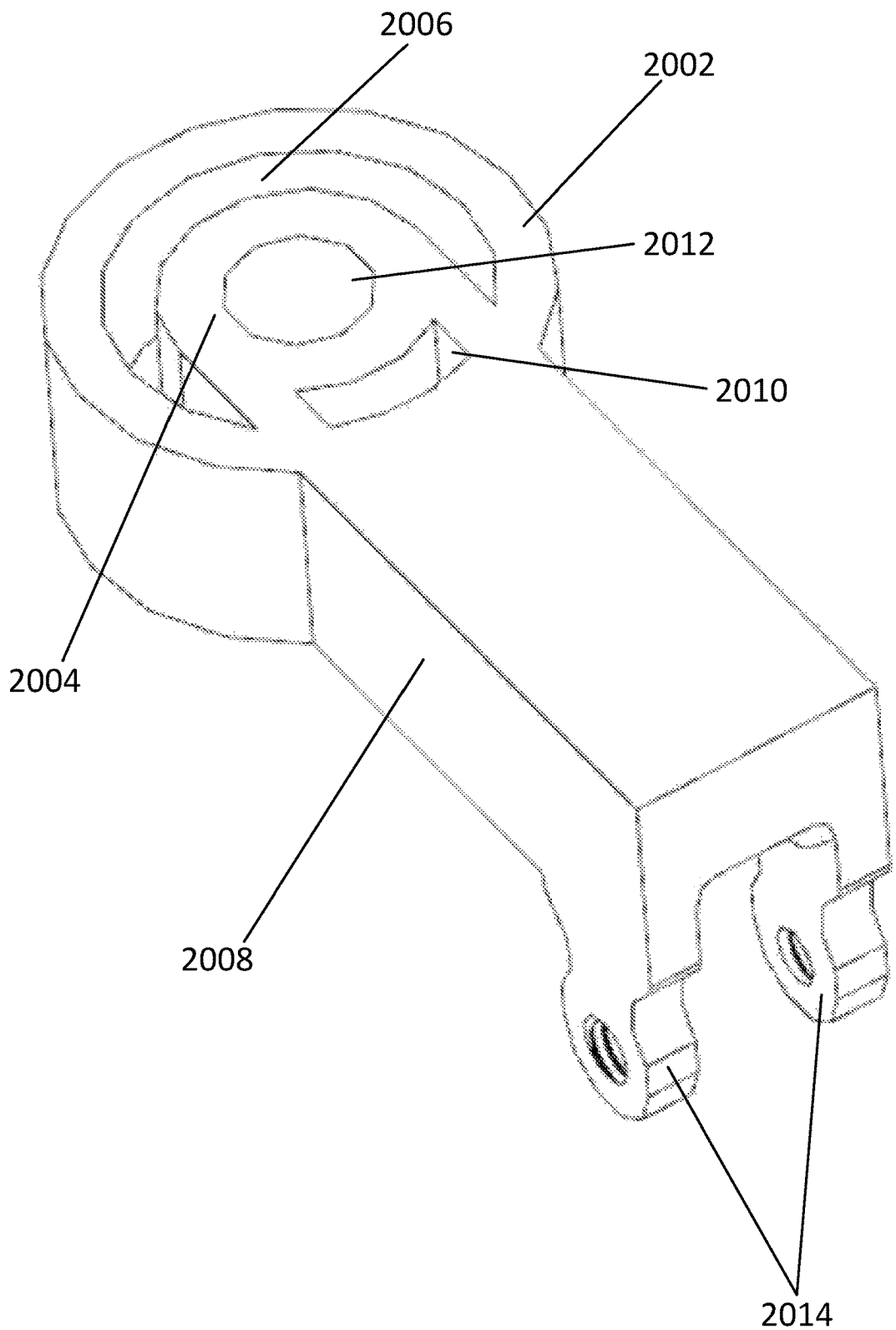
FIG. 20 illustrates a perspective view of an embodiment of a fixed arm of the external fixation strut depicted in FIG. 2 in accordance with one aspect of the present disclosure.

FIG. 20 illustrates a perspective view of an embodiment of the fixed arm 208. As shown, the fixed arm 208 may include a first member, portion, or coupling component 2002 and a second member, portion, or coupling component 2004. The first and second coupling components 2002 and 2004 may be separated by a first gap or opening 2006. The first and second coupling components 2002 and 2004 may be connected to an arm component 2008. The fixed arm 208 may further include a second gap or opening 2010. It should be understood that the fixed arm 208 may be formed by any suitable manner, for example, as an integral member with one or more openings formed therein.

In one embodiment, the first opening 2006 may be shaped and configured to receive the first body component 1504 of the main body 202 and the second opening 2010 may be shaped and configured to receive the second body component 1506 of the main body 202. Accordingly, when the fixed arm 208 is connected to the main body 202, the first coupling component 2002 may be positioned on an outside of the main body 202 and the second coupling component 2004 may be positioned within an inside of the main body 202.

As further shown in FIG. 20, the second coupling component 2004 may include a hole or opening 2012. The threaded portion 205 of the threaded rod 204 may be positioned within the hole 2012. The hole 2012 may be unthreaded such that the threaded rod 204 may rotate and/or move within the hole 2012 unhindered such that, rotation of the threaded rod 204 does not affect the location of the fixed arm 208. Accordingly, as the threaded rod 204 is rotated (e.g., by rotation of the actuator 206), the fixed arm 208 may remain in a fixed positioned attached to the main body 202.

Figure 31:
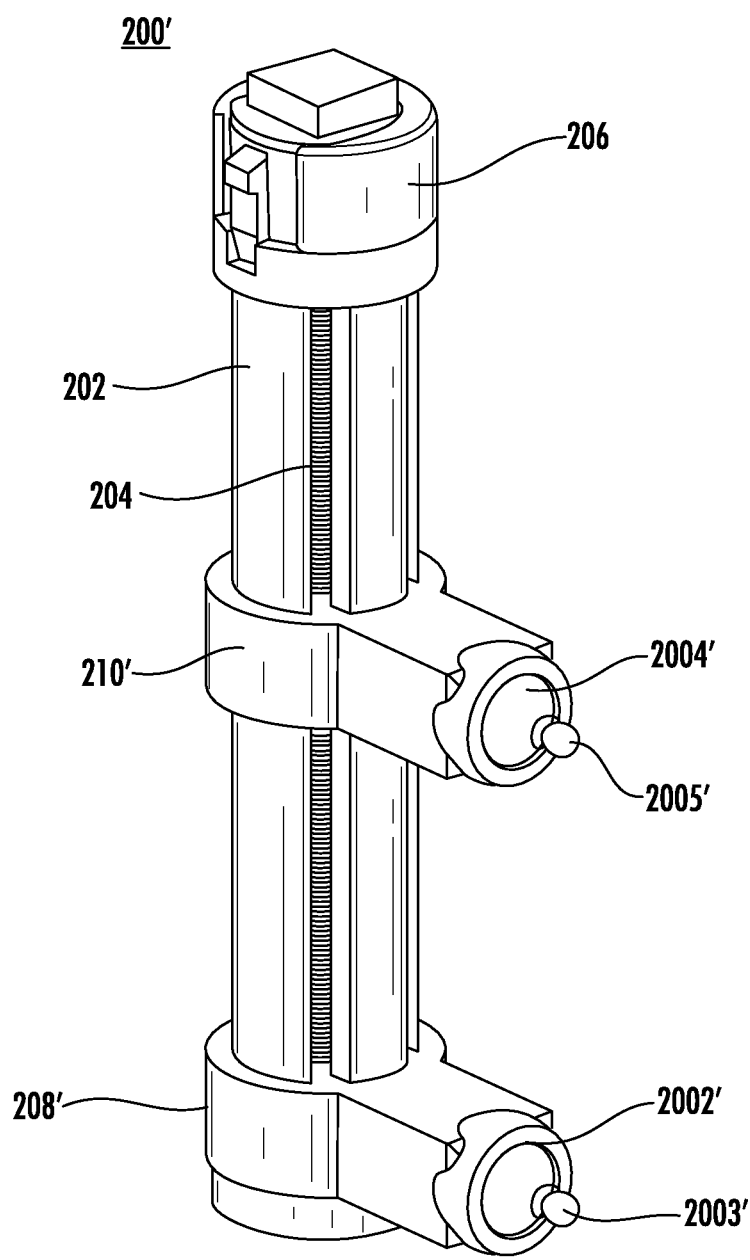
FIG. 31 illustrates a perspective view of an alternative embodiment of an external fixation strut in accordance with one aspect of the present disclosure.

As shown, the arm component 2008 may extend away from the first and second coupling components 2002 and 2004. The arm component 2008 may include one or more components for connecting the fixed arm 208 to a ring or other component of a bone alignment device. The arm component 2008 may include any suitable type of one or more components for connecting the fixed arm 208 to a ring or other component of a bone alignment device. For example, the arm component 2008 may include any combination of hinges, ball joints, universal joints, and fixed joints for connecting to a ring or other component of a bone alignment device. In an embodiment, the fixed arm 208 may include connector components 2014. The connector components 2014 may be connected to a joint such as, for example, the universal joint 216. For example, referring to FIG. 31, first and second arms (e.g., the fixed and moving arms) 208', 210' of the strut 200' may include a ball joint 2002', 2004' at an end thereof. In use, the ball joints 2002', 2004', and hence the fixed and moving arms 208', 210' may be directly coupled to the first and second rings 102, 104. That is, in one embodiment, the first and second rings 102, 104 may include holes formed in the side surfaces thereof for receiving a projection 2003', 2005' extending from the ball joints 2002', 2004' incorporated into the fixed and moving arms 208', 210' of the strut 200'.

Figure 21:
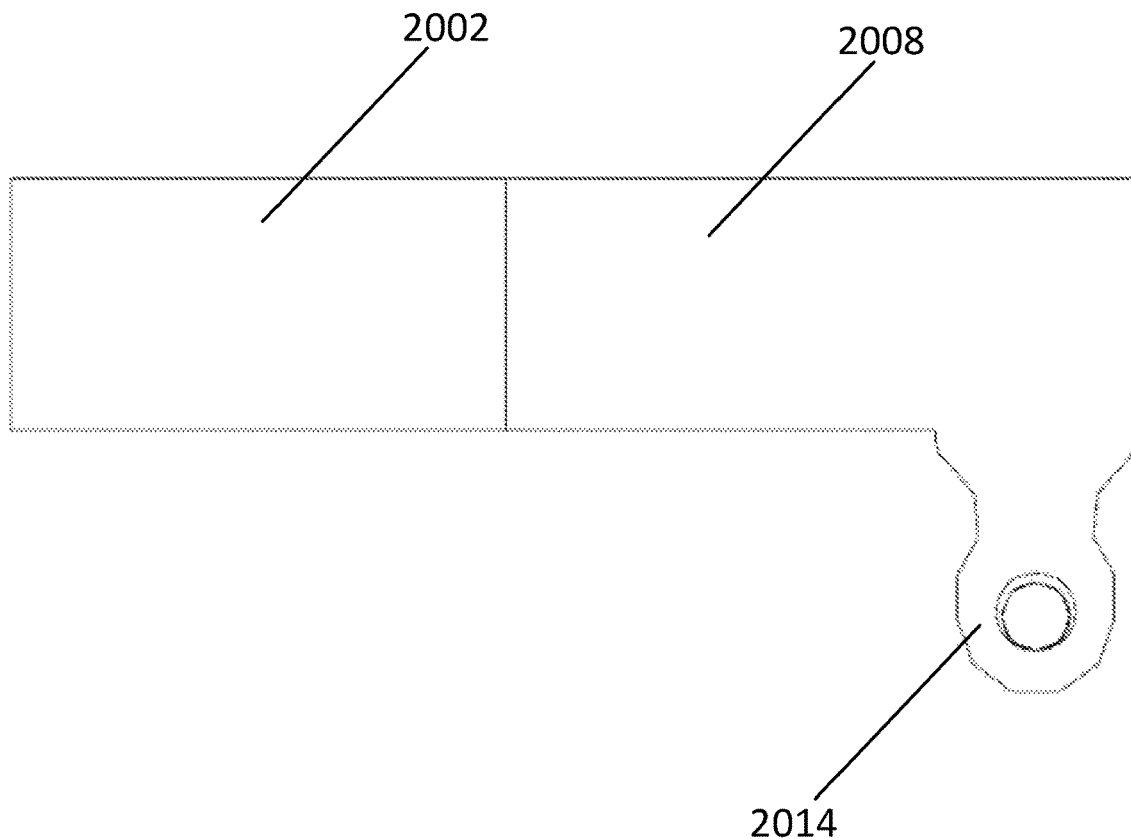
FIG. 21 illustrates a side view of the fixed arm depicted in FIG. 20.

FIG. 21 illustrates a side view of the fixed arm 208. FIG. 21 shows the relative arrangement of the first coupling component 2002, the arm component 2008, and the connector components 2014.

Figure 22:
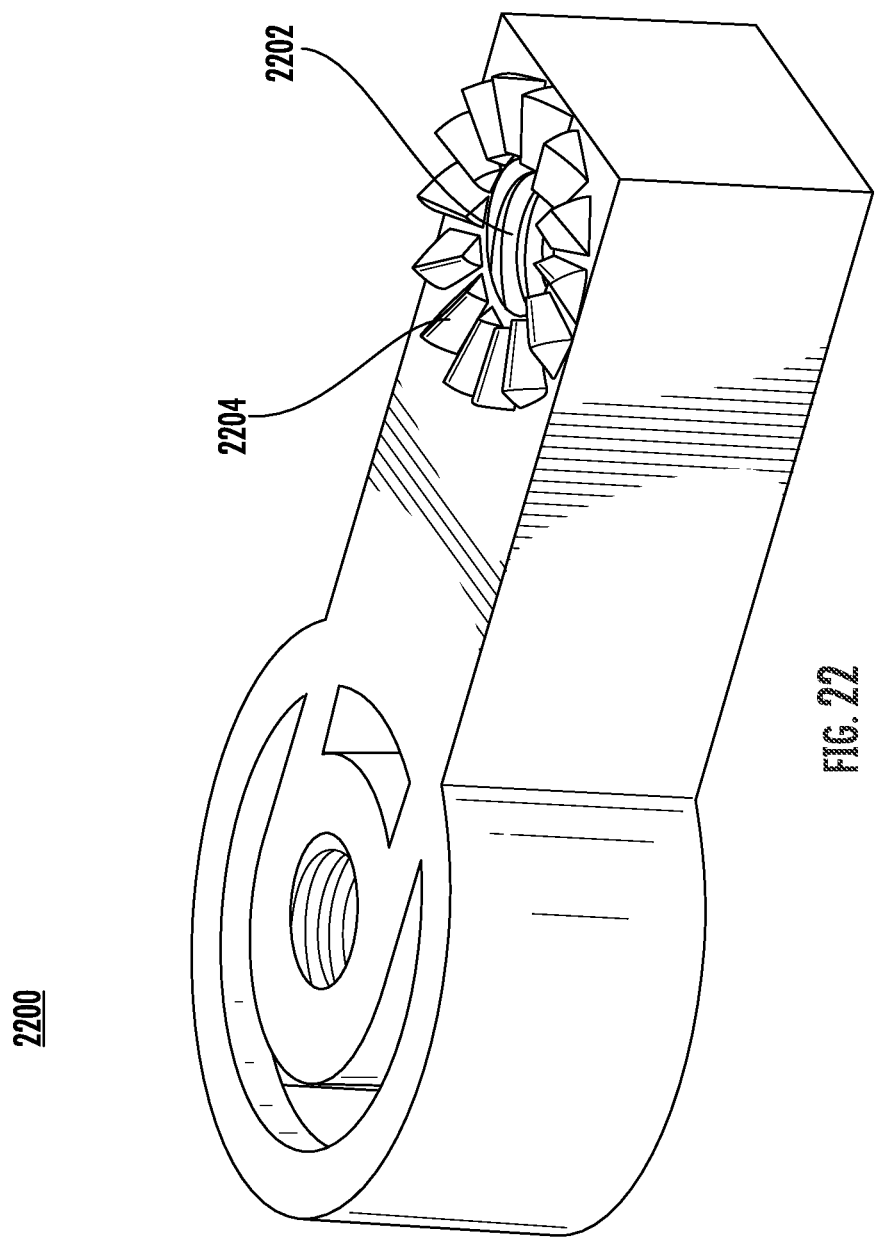
FIG. 22 illustrate an alternative embodiment of a moving arm of the external fixation strut depicted in FIG. 2 in accordance with one aspect of the present disclosure.

FIG. 22 illustrates an alternative embodiment of a moving arm 2200. The moving arm 2200 may represent an alternative arrangement, form factor, and/or design of the moving arm 210. In various embodiments, the moving arm 2200 may include the same or similar components and may provide the same or similar functionalities as the moving arm 210. Further, in various embodiments, the moving arm 2200 may be attached to the main body 202 and may operate in a similar manner as the moving arm 210. Accordingly, the external fixation strut 200 may be alternatively implemented with or may alternatively include the moving arm 2200.

As shown in FIG. 22, the moving arm 2200 may include a threaded hole 2202 and raised cleats 2204. The raised cleats 2204 may be positioned around the threaded hole 2202. The threaded hole 2202 allows the moving arm 2200 to be attached to a ring or base of a bone alignment device with a bolt. The raised cleats 2204 may fix the axial rotation of the moving arm 2200 relative to the ring or base of the bone alignment device to which the moving arm 2200 may be attached.

Figure 23:
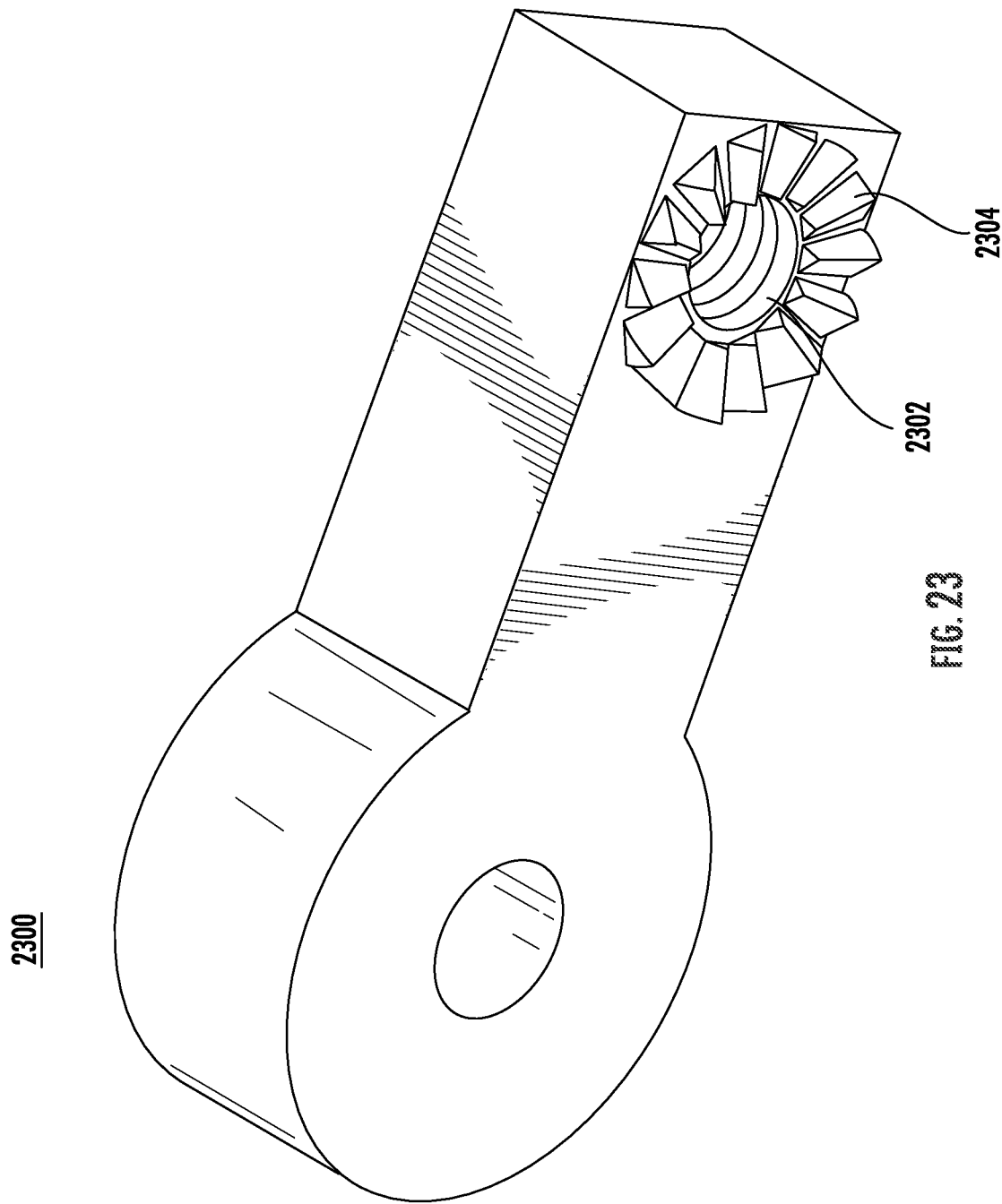
FIG. 23 illustrate an alternative embodiment of a fixed arm of the external fixation strut depicted in FIG. 2 in accordance with one aspect of the present disclosure.

FIG. 23 illustrates an alternative embodiment of a fixed arm 2300. The fixed arm 2300 may represent an alternative arrangement, form factor, or design of the fixed arm 208. In various embodiments, the fixed arm 2300 may include the same or similar components and may provide the same or similar functionalities as the fixed arm 208. Further, in various embodiments, the fixed arm 2300 may be attached to the main body 202 and may operate in a similar manner as the fixed arm 208. Accordingly, the external fixation strut 200 may be alternatively implemented with or may alternatively include the fixed arm 2300.

As shown in FIG. 23, the fixed arm 2300 may include a threaded hole 2302 and raised cleats 2304. The raised cleats 2304 may be positioned around the threaded hole 2302. The threaded hole 2302 allows the fixed arm 2300 to be attached to a ring or base of a bone alignment device with a bolt. The raised cleats 2304 may fix the axial rotation of the fixed arm 2300 relative to the ring or base of the bone alignment device to which the fixed arm 2300 may be attached. The orientation of the raised cleats 2204 and 2304 as shown in FIGS. 22 and 23 is not limiting as any roughened or cleated surface could serve to help prevent rotation of the of fixed arm 2200 and moving arm 2300 relative to the rings or external fixator bases.

Figure 24:
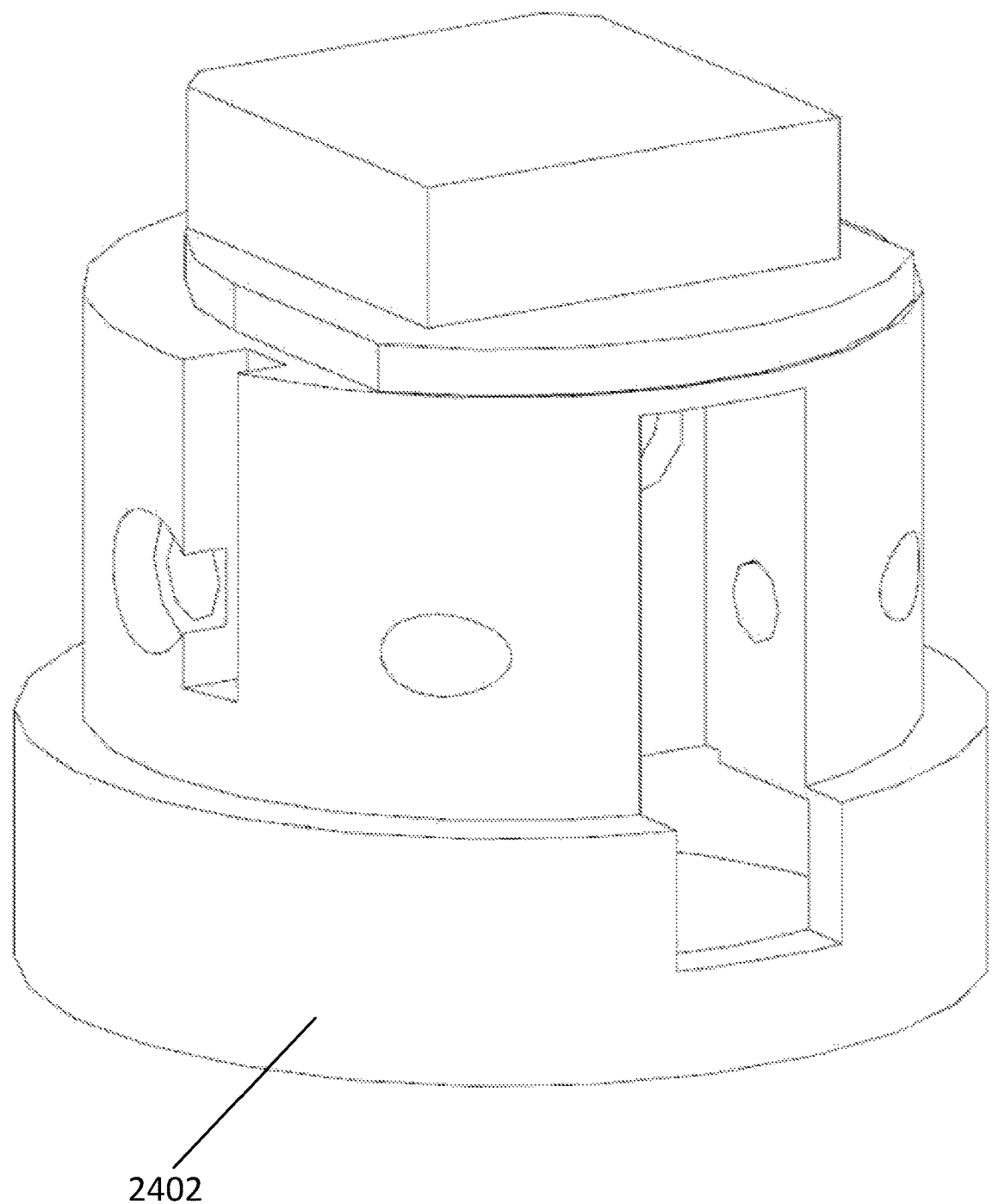
FIG. 24 illustrates a perspective view of an embodiment of an actuator of the external fixation strut depicted in FIG. 2 in accordance with one aspect of the present disclosure.

FIG. 24 illustrates a perspective view of an embodiment of the actuator 206. As shown, the actuator 206 may include a base 2402. The base 2402 may be positioned over the main body 202 and the threaded rod 204 as shown in FIGS. 2-6. The actuator 206 is not limited to the shape, size, and form factor depicted in FIG. 24.

Figure 25:
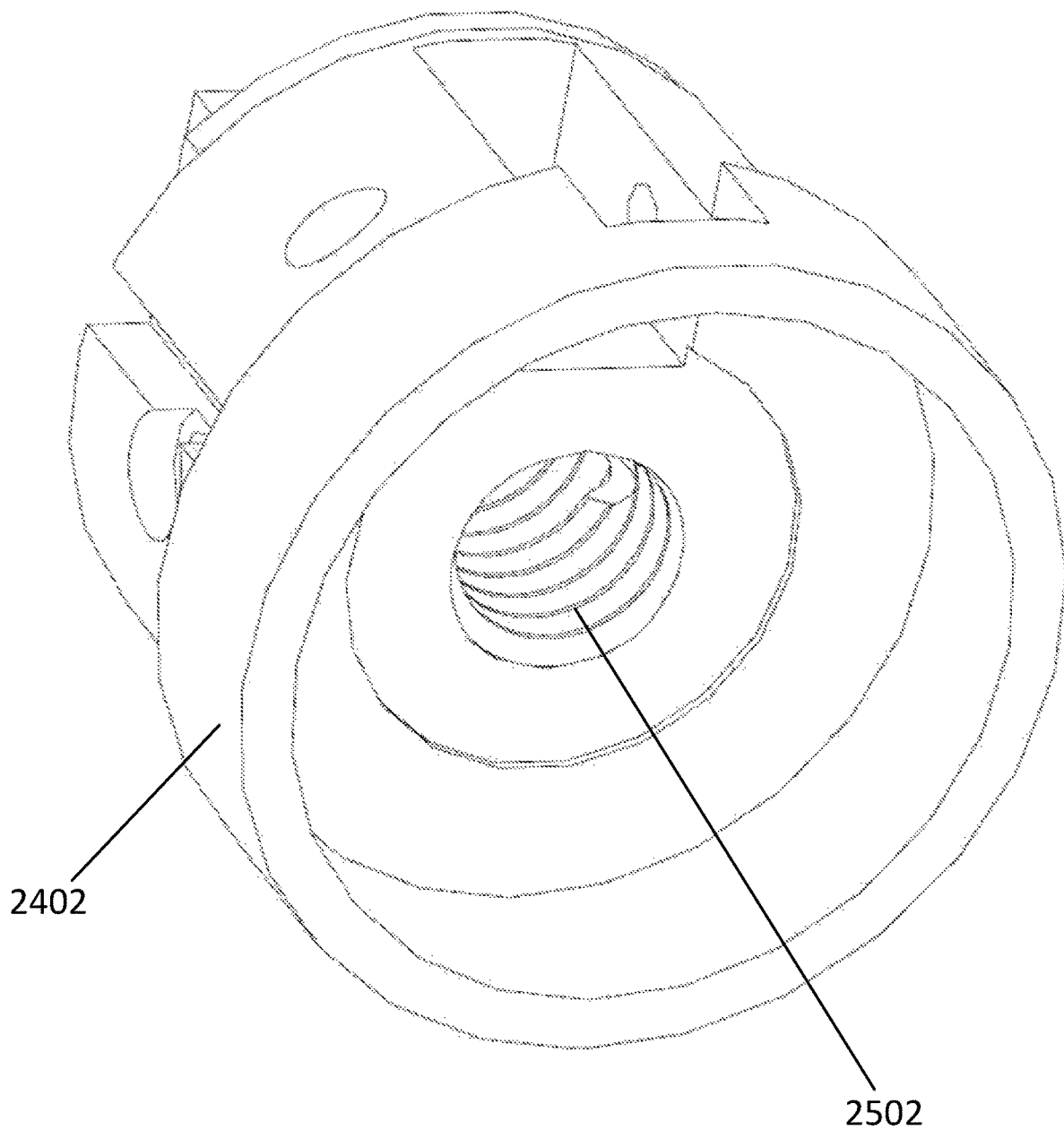
FIG. 25 illustrates an alternate perspective view of the actuator depicted in FIG. 24.

FIG. 25 illustrates an alternate perspective view of the actuator 206. Specifically, FIG. 25 shows an underside view of the actuator 206. As shown, the actuator 206 may include a threaded hole 2502 for receiving an end of the threaded rod 204. After the threaded rod 204 is threaded into the threaded hole 2502, rotating the actuator 206 may cause the threaded rod 204 to rotate, which, in turn, causes the moving arm 210 to move relative to the main body 202 and the fixed arm 208. The direction of movement of the moving arm 210 may be determined by the direction of rotation of the actuator 206 and therefore the threaded rod 204. The actuator 206 may be fixed to the threaded rod 204 by any suitable mechanism now known or hereafter developed. For example, as shown and described herein, the actuator 206 may include a threaded hole for threadably engaging the threaded rod 204. Alternatively, it is envisioned that the actuator 206 may be coupled to the threaded rod by other mechanisms such as, for example, pins or the like such that rotation of the actuator 206 rotates the threaded rod 204.

The actuator 206 may include any suitable locking component or mechanism now known or hereafter developed. The locking mechanism may prevent unintended rotation of the actuator 206. The locking mechanism may include any type of locking mechanism including, for example, any combination of ball detent, spring plunger, and poker chip.

Figure 26:
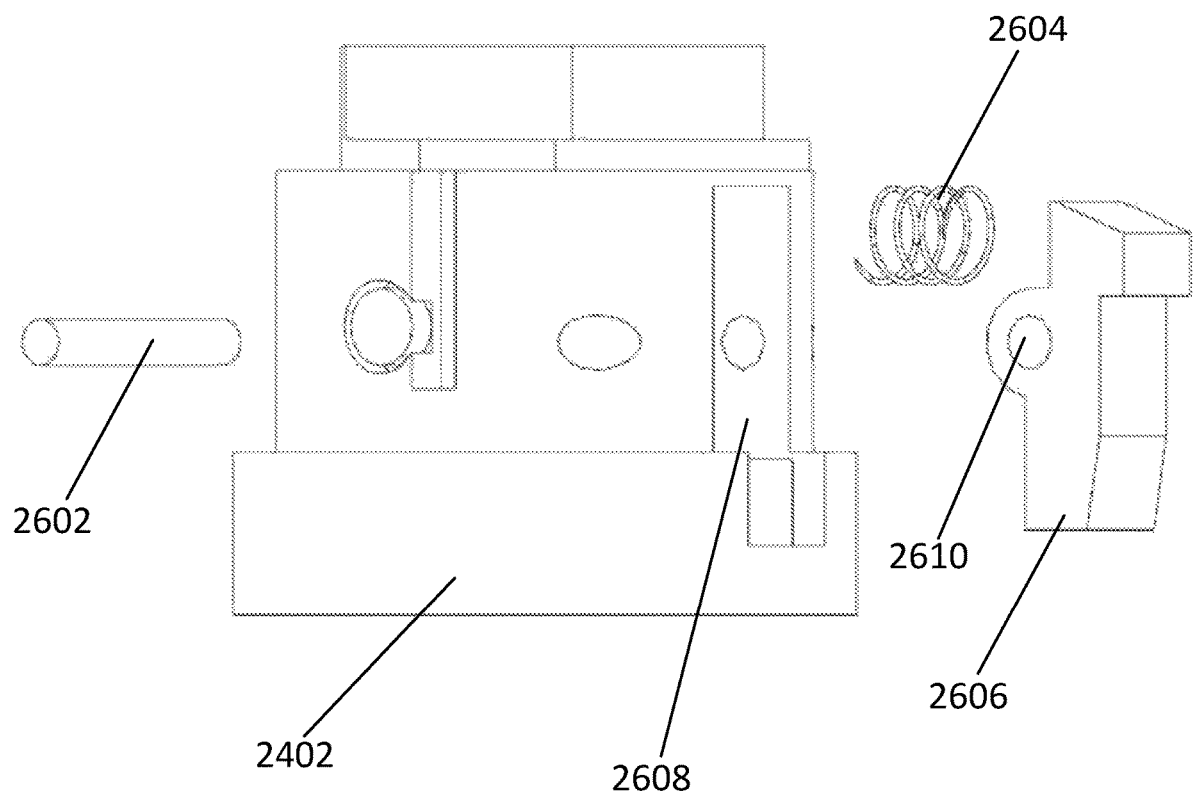
FIG. 26 illustrates an exploded view of an embodiment of an actuator of the external fixation strut depicted in FIG. 2 having a locking mechanism in accordance with one aspect of the present disclosure.
Figure 27:
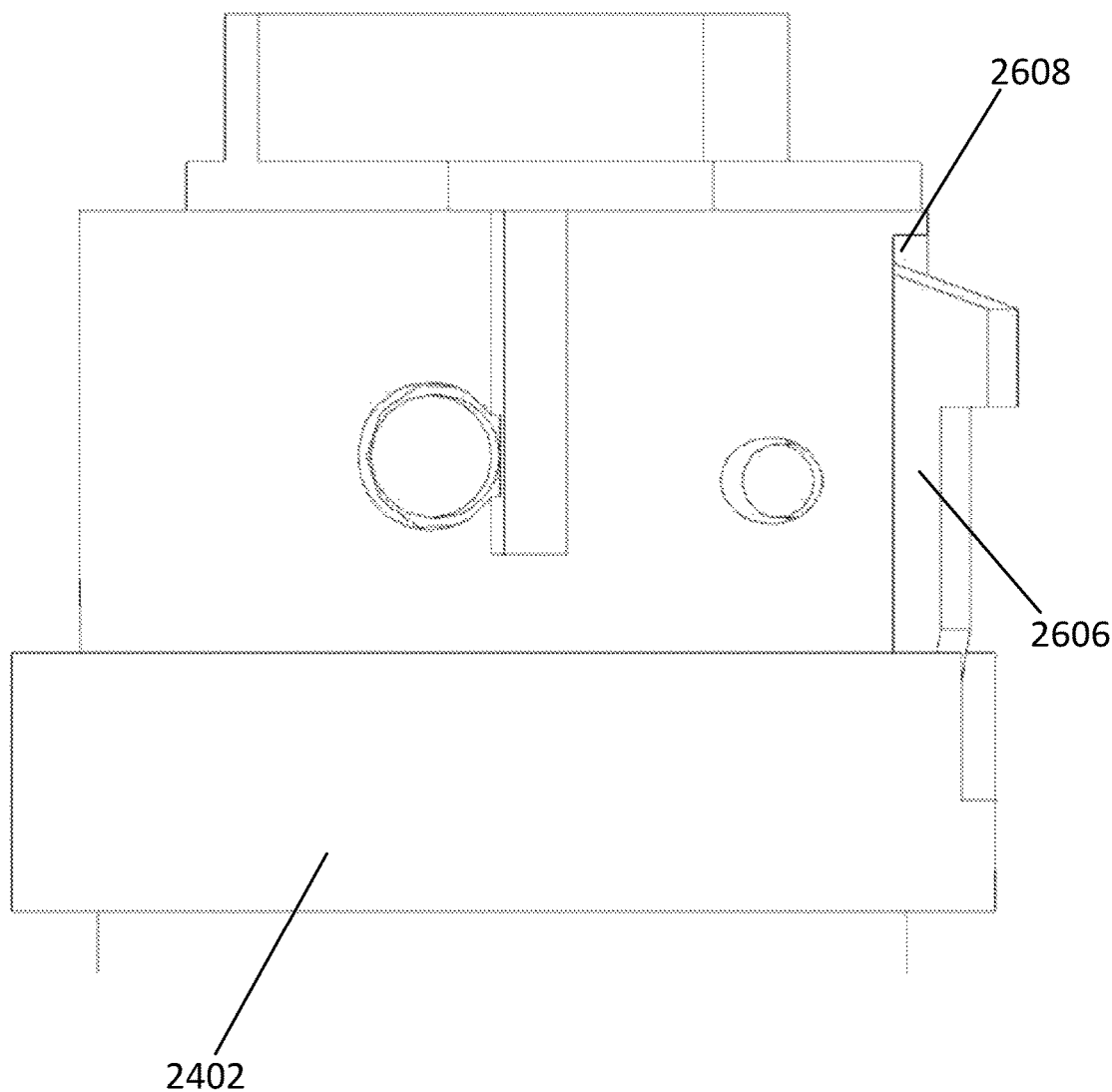
FIG. 27 illustrates an alternate view of the actuator of FIG. 26, the locking mechanism being in a locked configuration.
Figure 28:
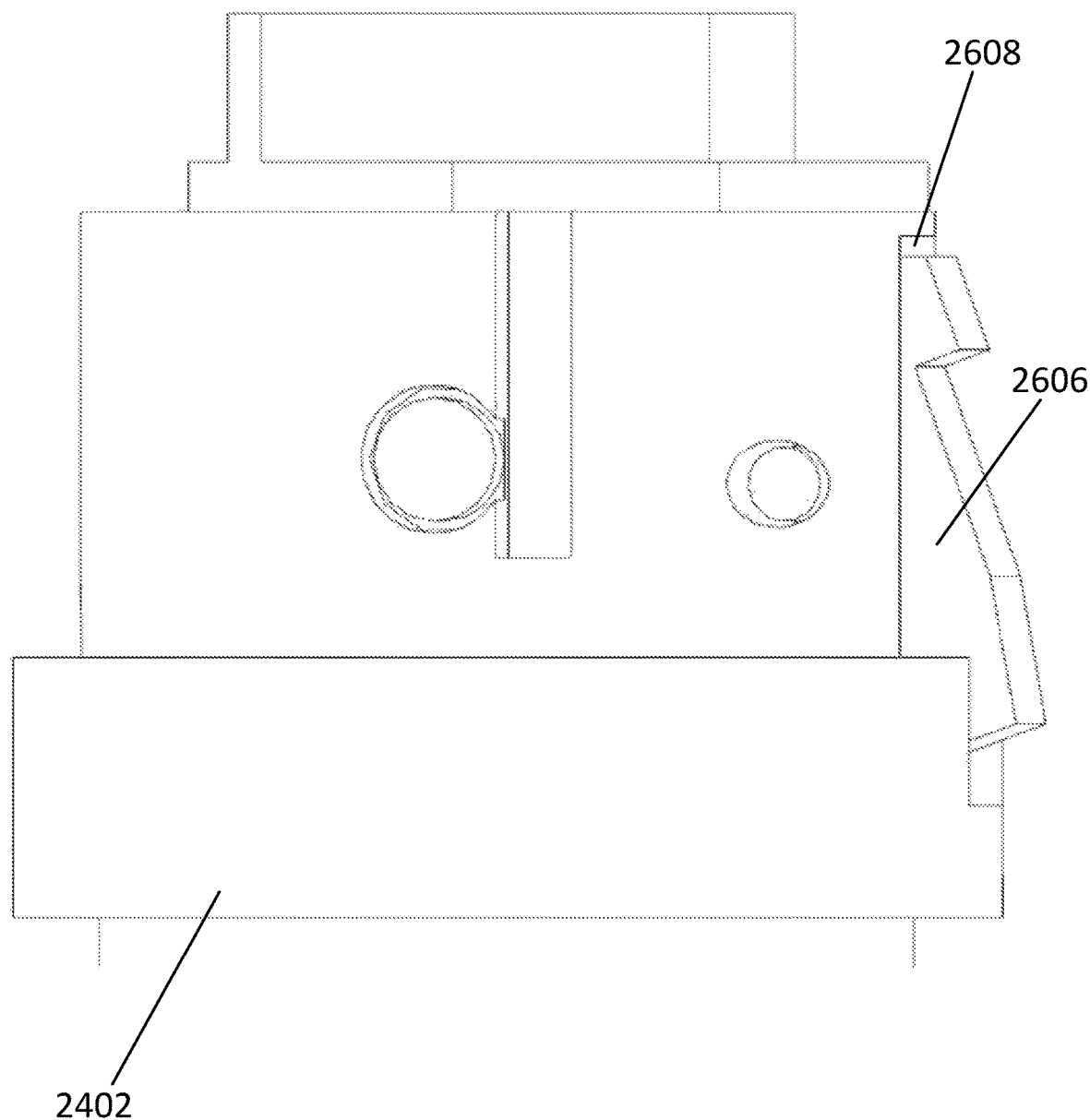
FIG. 28 illustrates the actuator of FIG. 26, the locking mechanism being in an unlocked configuration.

For example, referring to FIGS. 26-28, an example of an embodiment of the actuator 206 with an example locking mechanism is disclosed. FIG. 26 illustrates an exploded view of the actuator 206 with the example locking mechanism. As shown, the locking mechanism may include a pin 2602, a spring 2604, and a lever arm 2606. The lever arm 2606 may be positioned within an opening or cavity 2608 formed in the actuator 206. When the lever arm 2606 is positioned in the cavity 2608, the pin 2602 may be slotted through an opening or hole 2610 of the lever arm 2604 to allow the lever arm 2604 to pivot.

FIG. 27 illustrates the actuator 206 with the example locking mechanism in a locked configuration. As shown in FIG. 27, the lever arm 2606 is positioned within the cavity 2608. FIG. 28 illustrates the actuator 206 with the example locking mechanism in an unlocked configuration. As shown in FIG. 28, the lever arm 2606 rotates or translates out of the cavity 2608. A user of the external fixation strut 200 may manipulate the position of the lever arm 2606 to lock and unlock the actuator 206. In use, in the locked configuration, the lever arm 2606 is arranged and configured to prevent rotation of the actuator 206. For example, in one embodiment, the lever arm 2606 is arranged and configured to interact with the main body 202 or any other components of the strut to prevent rotation of the actuator 206 and hence the threaded rod 204 relative to the main body 202. In the unlocked position, the lever arm 2606 is arranged and configured to enable the actuator 206, and hence the threaded rod 204, to freely rotate. In one embodiment, the lever arm 2606 is biased to the locked position.

As described herein, the external fixation strut 200, including any variations described herein, may be used with any bone alignment device now known or hereafter developed. In general, any number of external fixation struts 200, including any variations described herein, may be used to connect two rings or bases of any type of bone alignment device as described herein.

Figure 29:
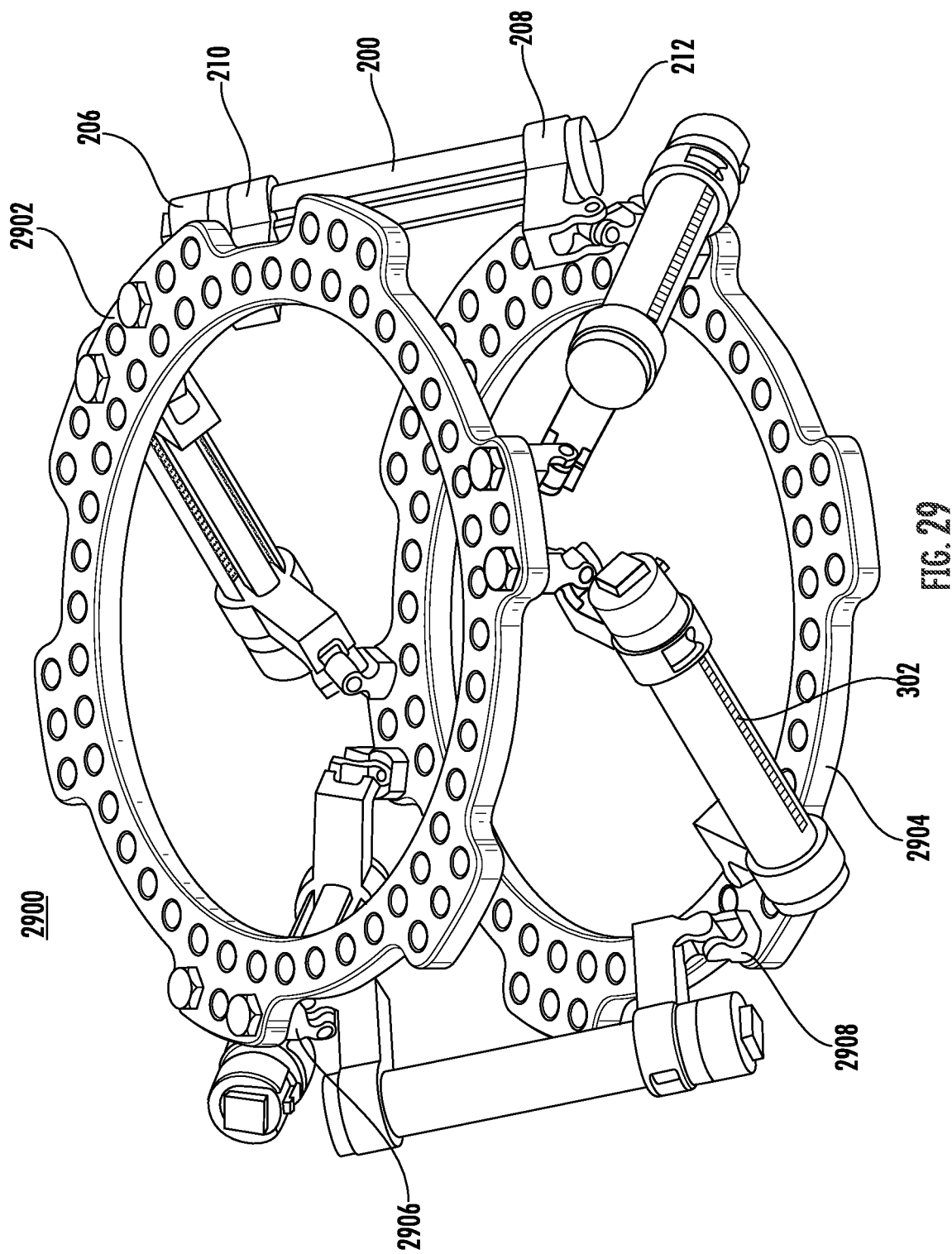
FIG. 29 illustrates a perspective view of an embodiment of a bone alignment device in accordance with one aspect of the present disclosure.

FIG. 29 illustrates an embodiment of a first bone alignment device 2900. The bone alignment device may include one or more of the external fixation struts 200. As shown in FIG. 29, the bone alignment device 2900 may form a hexapod having a circular, metal frame with a first ring 2902 and a second ring 2904 connected by six external fixation struts 200 (for simplicity, only one external fixation strut 200 is labeled). The external fixation strut 200 may be connected to the first ring 2902 through a first universal joint 2906 connected to the moving arm 210. The external fixation strut 200 may be connected to the second ring 2904 through a second universal joint 2908 connected to the fixed arm 208. As shown in FIG. 29, the external fixation struts 200 may be positioned on an outside of the first and second rings 2902 and 2904, thereby ensuring the first and second rings 2902 and 2904 may be spaced very close together.

As described herein, the external fixation struts 200 of the bone alignment device 2900 may expand the minimum and maximum working range of the bone alignment device 2900 while providing a user adjusting the spacing of the first and second rings 2902 and 2904 a single measurement scale 302 on each external fixation strut 200 to enhance usability and reliability.

Figure 30:
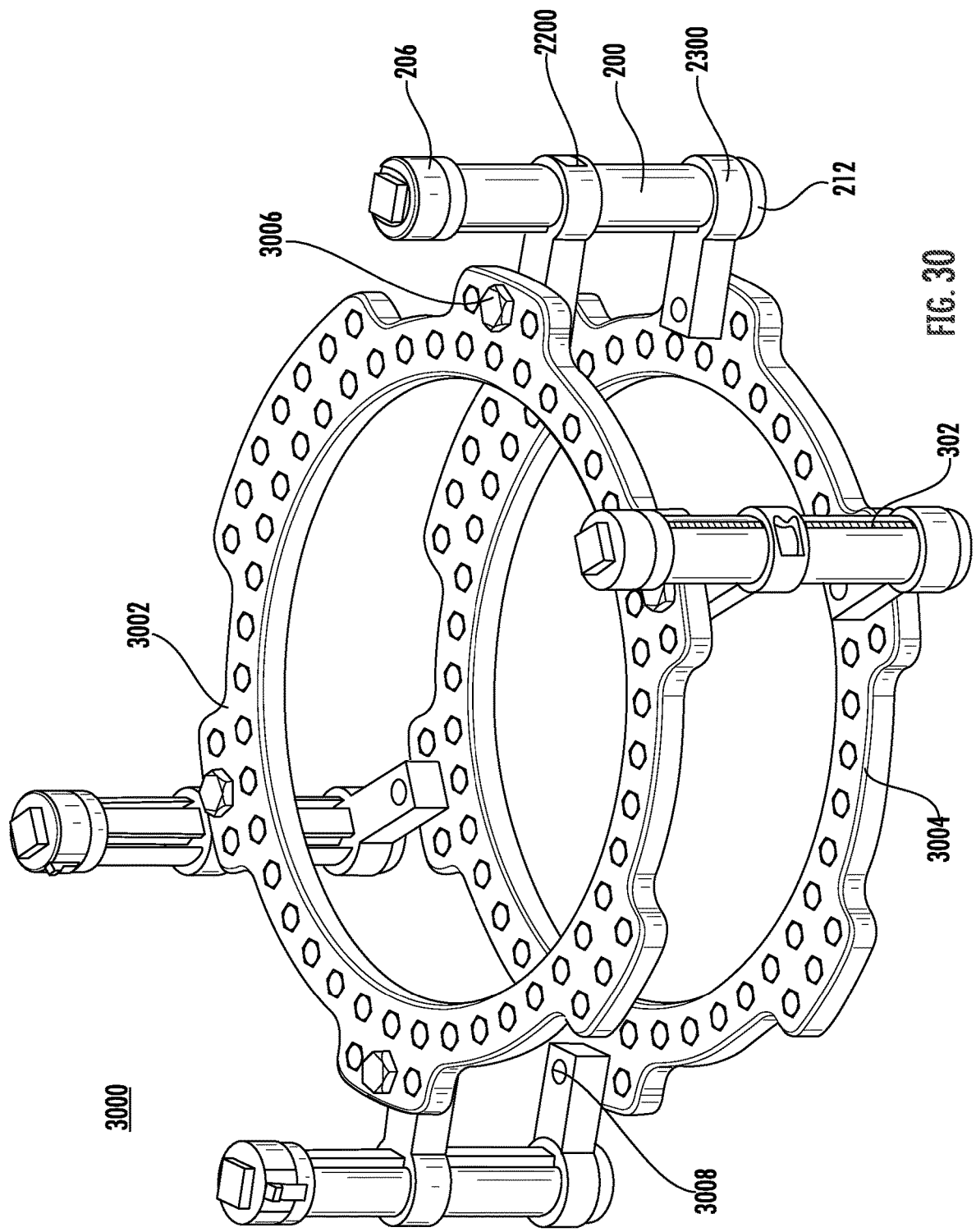
FIG. 30 illustrates a perspective view of an alternate embodiment of a bone alignment device in accordance with one aspect of the present disclosure.

FIG. 30 illustrates an embodiment of a second bone alignment device 3000. The bone alignment device 3000 may include one or more of the external fixation struts 200. As shown in FIG. 30, the bone alignment device 3000 may have a circular, metal frame with a first ring 3002 and a second ring 3004 connected by four external fixation struts 200 (for simplicity, only one external fixation strut 200 is labeled). The external fixation strut 200 may include the alternative moving arm 2200 and the alternative fixed arm 2300. The external fixation strut 200 may be connected to the first ring 3002 through a first bolt 3006 connected to the alternative moving arm 2200. The external fixation strut 200 may be connected to the second ring 3004 through a second bolt 3008 connected to the alternative fixed arm 2300. As shown in FIG. 30, the external fixation struts 200 may be positioned on an outside of the first and second rings 3002 and 3004, thereby ensuring the first and second rings 3002 and 3004 may be spaced very close together.

As described herein, the external fixation struts 200 of the bone alignment device 3000 may expand the minimum and maximum working range of the bone alignment device 3000 while providing a user adjusting the spacing of the first and second rings 3002 and 3004 a single measurement scale 302 on each external fixation strut 200 to enhance usability and reliability.

In an embodiment, the external fixation strut 200 may include an identification (ID) such that each external fixation strut 200 attached to or forming part of a bone alignment device (e.g., the bone alignment devices 2900 and 3000) may be distinguished. In one embodiment, the ID may be a bar code or other scannable code. In one embodiment, the ID may include textual and/or graphical markers. In general, any suitable ID now known or hereafter developed that may be used to distinguish external fixation struts 200 may be used.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. An external fixation strut for use with an external fixation system, the external fixation strut comprising:
   a main body including: an interior cavity, a central longitudinal axis, a first body component, and a second body component, the first body component and the second body component extending along a longitudinal length of the main body and spaced apart such that component gaps are formed on either side of the second body component adjacent to the first body component;
   a threaded rod at least partially positioned within the interior cavity of the main body;
   an actuator operatively coupled to the threaded rod so that, in use, rotation of the actuator causes the threaded rod to rotate;
   a first fixed arm immovably coupled to the main body; and
   a second movable arm threadably coupled to the threaded rod so that, in use, rotation of the threaded rod causes the second movable arm to move relative to the first fixed arm between a maximum length position and a minimum length position;
   wherein each of the first fixed arm and the second movable arm include: a ring having an opening, a coupling component fixedly arranged within the ring and including a gap, and an arm extending laterally from the ring, the first body component passing through the opening, the second body component passing through the gap, the arm extending laterally from the ring so that the arm is perpendicular to the central longitudinal.

2. The external fixation strut of claim 1, wherein the first fixed arm is immovably coupled adjacent to a first end of the main body and the actuator is positioned adjacent to a second end of the main body.

3. The external fixation strut of claim 1, wherein the threaded rod includes a first end and a second end, the actuator is coupled to the first end of the threaded rod, the threaded rod includes a base portion formed at the second end thereof, the base portion being positioned adjacent to a first end of the main body when the threaded rod is positioned within the interior cavity of the main body.

4. The external fixation strut of claim 3, wherein the first end of the threaded rod opposite to the base portion is arranged and configured to extend beyond a second end of the main body when the base portion is adjacent to the first end of the main body, the actuator being arranged and configured to threadably engage the first end of the threaded rod extending beyond the second end of the main body.

5. The external fixation strut of claim 1, wherein the external fixation strut includes a single measurement scale positioned on an outer surface of the main body along a length of the main body, the measurement scale being arranged and configured to measure a distance between the first fixed arm and the second movable arm.

6. The external fixation strut of claim 5, wherein the second movable arm includes a window arranged and configured to display the measurement scale so that, in use, a user can view the measurement scale when the second movable arm is positioned over the measurement scale.

7. The external fixation strut of claim 1, wherein the opening is positioned between the coupling component and the ring;
   wherein, when the first fixed arm and the second movable arm are coupled to the main body, the ring is arranged and configured to be positioned about an outer surface of the main body and the coupling component is arranged and configured to be positioned within the interior cavity of the main body.

8. The external fixation strut of claim 1, further comprising a locking mechanism operatively associated with the actuator, the locking mechanism being arranged and configured to prevent rotation of the actuator and hence the threaded rod, thereby preventing movement of the second movable arm relative to the first fixed arm.

9. The external fixation strut of claim 8, wherein the locking mechanism is movably positioned between a first locked position and a second unlocked position, wherein, in the first locked position, the actuator is prohibited from rotating relative to the main body, and, in the second unlocked position, the actuator is freely rotatable relative to the main body.

10. The external fixation strut of claim 9, wherein the locking mechanism includes a pivotable lever arm, the pivotable lever arm being arranged and configured to be positioned within a cavity formed in the actuator, in use, in the first locked position the lever arm is arranged and configured to prevent rotation of the actuator relative to the main body and in the second unlocked position, the lever arm is arranged and configured to enable the actuator to freely rotate.

11. The external fixation strut of claim 1, wherein the gap is positioned between the coupling component and the first fixed arm or the second movable arm.

12. The external fixation strut of claim 1, wherein a threaded opening is arranged in the coupling component of at least one of the first fixed arm or the second movable arm for receiving the threaded rod.

13. The external fixation strut of claim 1, wherein the main body has a cylindrical shape, the first body component shaped to occupy a first portion of an internal perimeter of the main body, the second body component shaped to occupy a second portion of the internal perimeter.

14. An external fixation system comprising:
   a first ring;
   a second ring; and
   a plurality of external fixation struts, each of the plurality of external fixation struts including:
      a main body including: an interior cavity, a central longitudinal axis, a first body component, and a second body component, the first body component and the second body component extending along a longitudinal length of the main body and spaced apart such that component gaps are formed on either side of the second body component adjacent to the first body component;
      a threaded rod at least partially positioned within the interior cavity of the main body;
      an actuator operatively coupled to the threaded rod so that, in use, rotation of the actuator causes the threaded rod to rotate;

a first fixed arm immovably coupled to the main body; and a second movable arm threadably coupled to the threaded rod so that, in use, rotation of the threaded rod causes the second movable arm to move relative to the first fixed arm between a maximum length position and a minimum length position;

wherein each of the first fixed arm and the second movable arm include: a coupling ring having an opening, a coupling component fixedly arranged within the coupling ring and including a gap, and an arm extending laterally from the coupling ring, the first body component passing through the opening, the second body component passing through the gap, the arm extending laterally from the coupling ring so that the arm is perpendicular to the central longitudinal axis.

15. The external fixation system of claim 14, wherein the opening is positioned between the coupling component and the coupling ring;

wherein, when the first fixed arm and the second movable arm are coupled to the main body, the coupling ring is arranged and configured to be positioned about an outer surface of the main body and the coupling component is arranged and configured to be positioned within the interior cavity of the main body.

16. The external fixation system of claim 14, wherein the first fixed arm is immovably coupled adjacent to a first end of the main body and the actuator is positioned adjacent to a second end of the main body.

17. The external fixation system of claim 14, wherein the threaded rod includes a first end and a second end, the actuator is coupled to the first end of the threaded rod, the threaded rod includes a base portion formed at the second end thereof, the base portion being positioned adjacent to a first end of the main body when the threaded rod is positioned within the interior cavity of the main body.

18. The external fixation system of claim 17, wherein the first end of the threaded rod opposite to the base portion is arranged and configured to extend beyond a second end of the main body when the base portion is adjacent to the first end of the main body, the actuator being arranged and configured to threadably engage the first end of the threaded rod extending beyond the second end of the main body.

19. The external fixation system of claim 14, wherein the gap is positioned between the coupling component and the first fixed arm or the second movable arm.

20. The external fixation system of claim 14, wherein a threaded opening is arranged in the coupling component of at least one of the first fixed arm or the second movable arm for receiving the threaded rod.

* * * * *